United States Patent [19]
Van Nostrand et al.

[11] Patent Number: 5,270,165
[45] Date of Patent: Dec. 14, 1993

[54] METHOD OF DIAGNOSIS OF AMYLOIDOSES

[75] Inventors: William E. Van Nostrand, Irvine; Dennis D. Cunningham, Laguna Beach; Steven L. Wagner, La Jolla, all of Calif.

[73] Assignee: The Reagents of the University of California, Oakland, Calif.

[21] Appl. No.: 779,070

[22] Filed: Oct. 15, 1991

Related U.S. Application Data

[63] Continuation-in-part of Ser. No. 513,786, Apr. 24, 1990.

[51] Int. Cl.⁵ .............................................. G01N 33/53
[52] U.S. Cl. .................................... 435/7.1; 435/7.92; 435/7.93; 435/7.94; 435/7.95; 530/380; 530/387.9; 530/388.2
[58] Field of Search ............... 424/7.1; 435/6, 7.1, 435/7.92, 7.93–7.95; 436/88; 538/27; 530/380, 387

[56] References Cited

U.S. PATENT DOCUMENTS 4,837,164  6/1989  Glick .................................... 436/88

FOREIGN PATENT DOCUMENTS 304013  8/1988  European Pat. Off.
9014840  12/1990  PCT Int'l Appl.
9014841  12/1990  PCT Int'l Appl.

OTHER PUBLICATIONS

Isolation & Characterization of Amyloid P Component—Cerebral Amyoidosis Coria et al; Lab Investn 58, #4, pp. 454–458, 1988.
Van Nostrand, W. E., and Cunningham, D. D., J. Biol. Chem., 262:8508–8514 (1987).
Baker, J. B. et al., Cell, 21:37–45 (1980).
Wagner, S. L., et al. Biochemistry, 27:2173–2176 (1988).
Bradford, M. M., Anal. Biochem., 72:248–254 (1976).
Laemmli, Nature, 227:680–685 (1970).
Potempa, et al., Science, 241:699–700 (1988).
Homsen et al., Anal. Biochem. 46:489–501 (1972).
Rucinski et al., Blood, 53:47–62 (1979).
Wroblewski and Ladue, Proc. Soc. Exper. Biol. Med., 90:210–213 (1955).
Schmaier, et al., J. Clin. Invest., 75:242–250 (1985).
Laurell, Anal. Biochem., 15:45–52 (1966).
de Duve et al, Biochem J., 60:604–617 (1955).
Weissbach et al., J. Biol. Chem., 230:865–871 (1955).
Weidemann et al., Cell, 57:115–126 (1989).
Joachim et al., Nature, 341:226–230 (1989).
Palmert et al., Science, 241:1080–1084 (1988).
Kang et al., Nature, 325:733–736 (1987).
Goldgaber et al., Science, 235:877–884 (1987).
Ponte et al., Nature, 331:525–532 (1988).
Dyrks et al., The Embo Journal, 7:949–957 (1988).
Shivers et al., The Embo Journal, 7:1365–1370 (1988).
Tate-Ostroff et al., Proc. Natl. Acad. Sci. USA, 86:745–749 (1989).
Hooper, C., J. NIH Res., 1:88–93 (1989).
Carrell, R. W., Nature, 331:478–479 (1988).
Kitaguchi et al., Determination of Amyloid B Protein Precursors . . . , Bioch. Biophys. Res. Comm., 166:1453–1459 (1990).

(List continued on next page.)

Primary Examiner—Christine M. Nucker
Assistant Examiner—Jeffrey Stucker
Attorney, Agent, or Firm—Knobbe Martens Olson & Bear

[57]                ABSTRACT

A method of diagnosing a disease with cerebrovascular deposition of amyloid, including Alzheimer's disease, hereditary cerebral hemorrhage with amyloidosis-Dutch type and other amyloidoses, in a mammal is disclosed in which a sample of cerebrospinal fluid is obtained, the level of immunoreactivity toward a monoclonal antibody raised against native PN-2/βAPP or other amyloid precursor protein in the sample is measured, and this measured level is compared to the level of immunoreactivity toward this antibody in a sample from a normal subject. A lower level in the sample from the mammal indicates a likelihood of the disease.

35 Claims, 16 Drawing Sheets

```
                  10                  20                  30                  40
βAPP    M L P G L A L L L L A A W T A R A L E V P T D G N A G L L A E P Q I A M F C G R

PN-2                                        L E V P T D G N A G L L A E P Q I A M F C G R 50                  60                  70                  80
βAPP    L N M H M N V Q N G K W D S D P S G T K T C I D T K E G I L Q Y C Q E V Y P E L

PN-2    L N M F M N V Q N G K W D S D P S G T K T C I D T K E G I L Q Y
                ↑       ̲ ̲ ̲ ̲ ̲ ̲ ̲ ̲ ̲ ̲ ̲ ̲ ̲ ̲ ̲ ̲ ̲ ̲ ̲ ̲ ̲ ̲ ̲ ̲ ̲ ̲ ̲ ̲ ̲ ̲ ̲

90                 100                 110                 120
βAPP    Q I T N V V E A N Q P V T I Q N W C K R G R K Q C K T H P H F V I P Y R C L V G

PN-2                                                          T X P H F V I P Y R
                                                              ̲ ̲ ̲ ̲ ̲ ̲ ̲ ̲ ̲
```

OTHER PUBLICATIONS

Ghiso et al., Alzheimer's Disease Amyloid Presucsor Protein is Present in Senile Plaques and Cerebrospinal Fluid, Bioch. Biophys. Res. Comm., 163:430–437 (1989).

Weidemann et al., Identification, Biogenesis, and Localization of Precursors of Alzheimer's Disease A4 Amyloid Protein, *Cell,* 57:115–126 (1989).

Marotta, C.A., et al. *Proc. Natl. Acad. Sci. USA,* 86:337–341 (1989).

Grubb et al., "Abnormal Metabolism of y-Trace Alkaline Microprotein" *Medical Intelligence,* 311:1547–1549 (1984).

Nature—vol. 341 Oct. 12, 1989 "Protease nexin-II, a potent anti-chymotrypsin, shows identity to amyloid B-protein precursor".

Van Nostrand et al, *J. Biol. Chem.,* vol. 265, No. 17 pp. 9591–9594 (1990).

Prior et al., *Neuroscience Letters,* 124 (1991) 69–73.

Henriksson, et al., *Journal of Neurochemistry,* 1991 1037–1042.

Palmert, et al., *Neurology* 40 Jul. 1990 1028–1034.

Smith, et al, *Science,* vol. 248 1126–1128.

Van Nostrand, et al., *Science,* vol. 248, May 11, 1990 745–748.

FIG. 1

```
βAPP  M L P G L A L L L L A A W T A R A L E V P T D G N A G L L A E P Q I A M F C G R
                    10                  20                  30                40
PN-2                                    L E V P T D G N A G L L A E P Q I A M F C G R

βAPP  L N M H M N V Q N G K W D S D P S G T K T C I D T K E G I L Q Y C Q E V Y P E L
                    50                  60                  70                80
PN-2  L N M F M N V Q N G K W D S D P S G T K T C I D T K E G I L Q Y
           ↑

βAPP  Q I T N V V E A N Q P V T I Q N W C K R G R K Q C K T H P H F V I P Y R C L V G
                    90                  100                 110               120
PN-2                                                        T X P H F V I P Y R
```

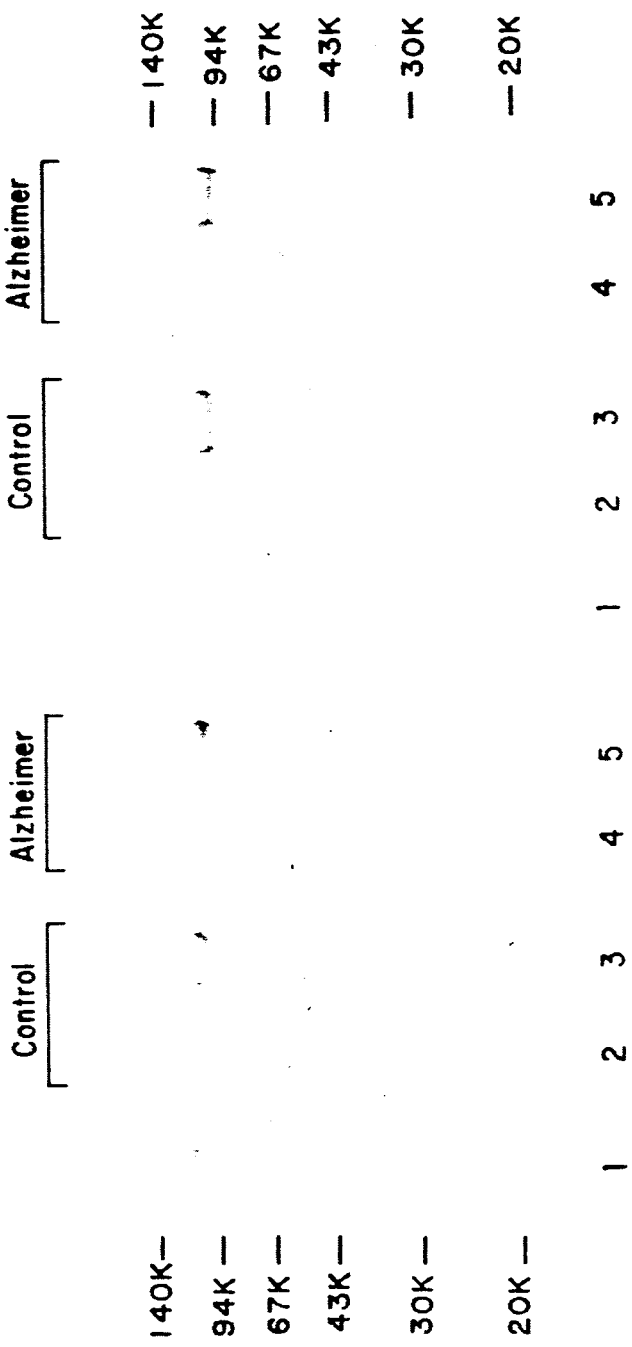

```
          10            20            30           40
βAPP  M L P G L A L L L L A A W T A R A L E V P T D G N A G L L A E P Q I A M F C G R
PN-2                                  L E V P T D G N A G L L A E P Q I A M F C G R 50            60            70           80
βAPP  L N M H M N V Q N G K W D S D P S G T K T C I D T K E G I L Q Y C Q E V Y P E L
PN-2  L N M F M N V Q N G K W D S D P S G T K T C I D T K E G I L Q Y
              ↑

90           100           110          120
βAPP  Q I T N V V E A N Q P V T I Q N W C K R G R K Q C K T H P H F V I P Y R C L V G
PN-2                                                T X P H F V I P Y R
```

METHOD OF DIAGNOSIS OF AMYLOIDOSES

NOTICE OF GOVERNMENT SUPPORT

This invention was made with Government support under Grant No. GM-31609 awarded by the National Institutes of Health. The Government has certain rights in this invention. American Cancer Society Grants CD 390 and BC 602/BE 22A provided further support for the development of this invention.

RELATED APPLICATIONS

The present application is continuation-in-part of U.S. patent application Ser. No. 513,786, filed Apr. 24, 1990, the disclosure of which is hereby incorporated in its entirety by reference thereto.

FIELD OF THE INVENTION

The present invention relates generally to the field of proteins associated with neural lesions. More specifically, the present invention relates to the detection of protease nexin-2 (hereinafter "PN-2") and other precursors to amyloid deposited in the cerebrovasculature.

BACKGROUND OF THE INVENTION

PN-2 is believed to be derived from β-amyloid precursor protein (hereinafter "βAPP"). As used herein, "βAPP" shall be used to designate the unprocessed, non-secreted forms of this amyloid precursor protein. Alternatively spliced forms of the two major mRNA transcripts for βAPP produce an unprocessed, non-secreted, membrane bound or possibly intracellular, full length protein of either 695 or 751 amino acids. Thus "$βAPP_{695}$" and "$βAPP_{751}$" are used herein to designate the 695 and 751 amino acid forms of the protein, respectively. $βAPP_{751}$ includes a 56 to 57 amino acid residue insert which is homologous to that of a "Kunitz-type" protease inhibitor which inhibits trypsin.

Each of the two major forms of βAPP is processed to form the two major secreted forms. It is the major secreted form of the 751 amino acid translation product which is referred to herein as "PN-2". The secreted form of the 695 amino acid protein is referred to herein as "$APP_{695sec}$".

For reasons which are discussed hereinbelow, the term "PN-2/βAPP" is used herein generically to refer to all proteins having sequence homology with the amyloid precursor protein.

Alzheimer's Disease (AD) produces a debilitating dementia for which no treatment is known, with no known reliable methods of diagnosis prior to autopsy. βAPP and its various processed forms are known to be associated with neural lesions of AD, as well as with Down's syndrome. AD is characterized by the accumulation of amyloid protein both intracellularly and extracellularly in the tissues of the brain, notably in neuritic plaques. The major protein subunit of these amyloid plaques has been identified as a polypeptide of about 4.5 kD having the ability to aggregate. This protein subunit is variously referred to as the amyloid β-protein or as amyloid A4, and is herein referred to as "A4".

The cDNA corresponding to the mRNA for the 695 amino acid βAPP lacking the Kunitz domain has been cloned and the nucleotide sequence determined. From the nucleotide sequence, the amino acid sequence has been predicted. The A4 peptide lies at residues 597 to 648 of the deduced amino acid sequence of $βAPP_{695}$.

A4 is thought to have its origin, through proteolytic cleavage, in βAPP. Release of the A4 unit is thought to occur by proteolysis of the precursor which may result from membrane damage. Because A4 is believed to be critical to the formation of amyloid plaques, there is a need for methods of preventing the release of A4.

Down's syndrome is a genetic disease which usually causes mental retardation and other symptoms. An unusually high number of people with Down's also develop Alzheimer's after the age of 40. Thus, there is a need for a treatment for Down's.

As discussed above, definitive diagnosis of Alzheimer's disease is only available at autopsy. Such diagnosis involves examination of brain tissue for extracellular neuritic plaques and intracellular tangles of microtubule-associated proteins and other cytoskeletal elements. The plaques are believed to start to form years before any clinical sign of Alzheimer's appears.

Many researchers believe that there is a correlation between the density of neuritic plaques and the severity of dementia. Thus, there is a need for preventing further development of neuritic plaques. If applied prior to the development of Alzheimer's symptoms, such a treatment, may thereby prevent onset of the disease.

Even without a treatment for Alzheimer's, an early diagnosis of the disease would allow physicians to rule out other causes of dementia. Moreover, in order to study the genetics of Alzheimer's it would be very useful to obtain a diagnosis of the disease prior to autopsy. More importantly, once treatments are developed, an early diagnosis may prove critical in the treatment's ability to improve mental functioning. Thus, there is a need for a method for the early diagnosis of Alzheimer's.

Currently, there is no reliable biochemical test available to assist in the diagnosis of Alzheimer's disease in live patients. Previous studies have produced conflicting data regarding the usefulness of measuring PN-2/βAPP in cerebrospinal fluid ("CSF") to assist in diagnosis of Alzheimer's disease. Three such studies (Kitaguchi et al., Biochem. Biophys. Res. Comm. 166:1453–1459 (1990), Weidemann et al., Cell 57:115–126 (1989) and Ghiso et al., Biochem. Biophys. Res. Comm. 163:430–437 (1989)) suggested that increased levels of PN-2/βAPP immunoreactivity can be found in the CSF of AD patients compared with controls. Another study (Palmert et al., Neurology 40:1028–1034 (1990)) found that the absolute and relative levels of PN-2/βAPP in cerebrospinal fluid overlapped between Alzheimer's disease patients and a control group. Yet another study (Henriksson et al., J. Neurochem 56:1037–1042 (1991)) indicated that while PN-2/βAPP levels were slightly reduced in AD relative to control, that measurement of PN-2/βAPP in CSF did not appear to be useful in diagnosing Alzheimer's disease.

Still another study (Prior et al., Neuroscience Letters 124:69–73 (1991)) indicated that the average amount of βAPP immunoreactivity in CSF was lower in a group of AD patients relative to a group of control subjects and was only slightly lower than a group of multiple infarct dementia patients. However, in this study, the range within each of these groups was very broad and overlapping between groups. Thus, this study failed to provide an indication of the presence of AD for any particular individual.

All of the foregoing studies of PN-2/βAPP immunoreactivity in CSF used polyclonal or monoclonal antibodies raised against synthetic proteins. These monoclonal antibodies lacked sufficient sensitivity to reliably determine differences in immunoreactivity among samples containing high levels of protein, such as CSF samples. The use of polyclonal antibodies results in cross-reactivity with other proteins. Thus, quantitation can only be achieved with these antibodies by performing immunoblots and excising major bands. The cross-reactivity of these antibodies with proteins other than PN-2/βAPP prevents them from being effectively used in enzyme-linked immunosorbent ("ELISA") assays. In light of the inability of previous studies to reliably detect Alzheimer's Disease, there remains a need for a reliable test to assist in the diagnosis of Alzheimer's Disease in live patients.

SUMMARY OF THE INVENTION

In accordance with one aspect of the present invention, there is provided a method of diagnosing AD in a mammal, comprising the steps of obtaining a sample of cerebrospinal fluid from the mammal, measuring the level of immunoreactivity toward a monoclonal antibody raised against native PN-2/βAPP in the sample, determining the level of immunoreactivity toward said antibody in a sample from a normal subject, and comparing the level measured in the sample from the mammal with the level determined in the normal subject, wherein a lower level in the CSF from the test mammal as compared to the normal subject indicates a likelihood of AD. In order to distinguish AD from non-Alzheimer's type dementia, the level measured in the sample from the mammal is compared with a level of immunoreactivity measured in a sample from a mammal suffering from a non-Alzheimer's type dementia. Preferably, the measurement of immunoreactivity is accomplished by means of an ELISA or immunoblot assay, and the CSF is collected by lumbar puncture. In a preferred ELISA assay, microtiter plates coated with a cationic substance are used.

In another aspect of the present invention, there is provided a method of diagnosing AD in a mammal, comprising the steps of obtaining a sample with a volume less than 100 µl of cerebrospinal fluid from the mammal, measuring the level of PN-2/βAPP in the sample, determining the level of PN-2/βAPP in a sample of the same volume of CSF from a normal subject, and comparing the level of PN-2/βAPP measured in the sample with the level measured in the normal subject, wherein a lower level in the CSF from the test mammal as compared to the normal subject indicates a likelihood of AD. Preferably, the sample has a volume in the range of 2 µl to 20 µl and more preferably in the range of 2 µl to 10 µl. The measuring step preferably is done on unconcentrated, nondialyzed CSF.

In still another aspect of the present invention, there is provided a method of diagnosing a disease associated with cerebrovascular deposition of amyloid in a mammal, comprising: identifying an amyloid precursor protein which is the precursor to the amyloid deposited in the cerebrovasculature of mammals with the disease, obtaining a sample of cerebrospinal fluid from the mammal, measuring the level of immunoreactivity toward an antibody raised against the amyloid precursor protein in the sample, determining the level of immunoreactivity toward the antibody in a sample from a normal subject, and comparing the level in the sample from the mammal with the level measured in a normal subject, wherein a lower level in the CSF from the test mammal as compared to the normal subject indicates a likelihood of the disease. In one aspect of this method, the disease is AD or hereditary cerebral hemorrhage with amyloidosis-Dutch type ("HCHWA-D") and the amyloid precursor protein is PN-2/βAPP. In another aspect, the disease is HCHWA-I and the amyloid precursor protein is cystatin-C. The identification step preferably comprises obtaining a sample of cerebrovascular amyloid deposits from a mammal suffering from the disease, and identifying amyloid precursor proteins found therein. The identifying step can comprise biochemical characterization of the sample of cerebrovascular deposits. Alternatively, this step can also comprise measuring immunoreactivity in the sample of amyloid deposits to a variety of antibodies raised against different amyloid precursor proteins, and identifying an amyloid precursor protein in which significant levels of immunoreactivity are found.

In still another aspect of the present invention, there is provided a method of diagnosing a disease associated with cerebrovascular deposition of PN-2/βAPP in a mammal, comprising: obtaining a sample of cerebrospinal fluid from the mammal, determining the level of PN-2/βAPP lacking the Kunitz protease inhibitory domain in the sample, determining the level of PN-2/βAPP lacking the Kunitz protease inhibitory domain in a sample from a normal subject, and comparing the level measured of PN-2/βAPP lacking the Kunitz protease inhibitory domain in the sample with the level of PN-2/βAPP lacking the Kunitz protease inhibitory domain in a sample from a normal subject, wherein a lower level measured in the sample from the test mammal as compared to the normal subject indicates a likelihood of the disease. In one embodiment, the level of PN-2/BAPP lacking the Kunitz protease inhibitory domain in the sample is determined by subtracting the level of Kunitz protease inhibitory domain containing form of PN-2/βAPP from the total level of PN-2/βAPP. The determination step of the level of Kunitz protease inhibitory domain containing form of PN-2/βAPP step can comprise the performance of an assay for protease:PN-2/βAPP complex formation.

within the CA1 region of the hippocampus. Solid arrows point to pyramidal neurons. Vibratome section (40 μm) viewed by Nomarsky interference microscopy. X1,000.

Figure 4:
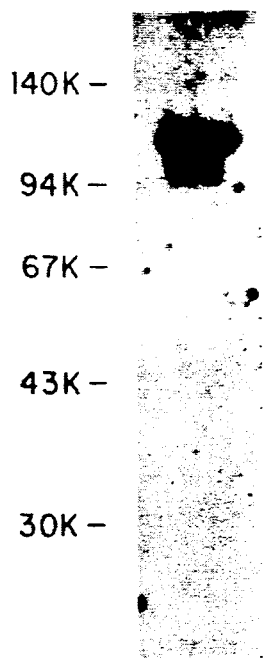

FIG. 4 shows the binding of $^{125}$I-chymotrypsin to purified secreted forms of βAPP/PN-2 after being subjected to SDS-PAGE and transferred to a nitrocellulose membrane.

Figure 5B:
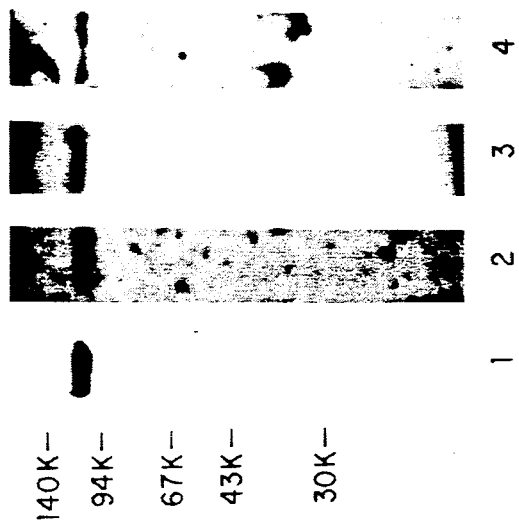
Figure 5A:
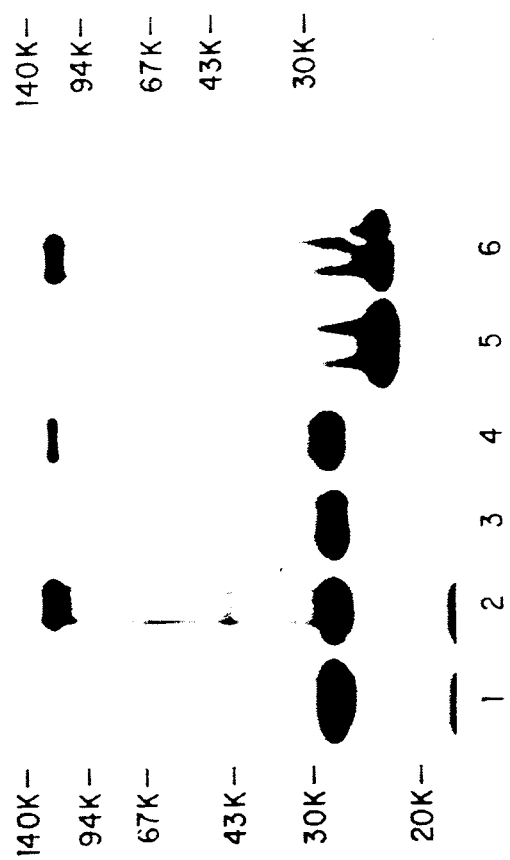

FIGS. 5a and 5b show $^{125}$I-protease-PN-2 complex formation. Panel A: 500 ng of purified PN-2 was incubated with 25 ng of $^{125}$I-labeled protease for 15 minutes at 37.C. The incubation mixtures were then analyzed for protease-PN-2 complexes by 10% SDS-PAGE without prior boiling of the samples and subsequent autoradiography. Lane 1, EGF BP; lane 2, EGF BP+PN-2; lane 3, NGF-γ; lane 4, NGF-γ30 PN-2; lane 5, trypsin; lane 6, trypsin+PN-2. Panel B: 1 μg aliquots of purified PN-2 were subjected to SDS-PAGE; completed gels were transferred to nitrocellulose membranes, incubated with $^{125}$I-labeled protease, washed and autoradiography was performed. PN-2 labeled with: lane 1, $^{125}$I-chymotrypsin; lane 2, 125I-factor XIa; lane 3, 125I-plasmin; lane 4, $^{125}$I-chymase.

Figure 6:
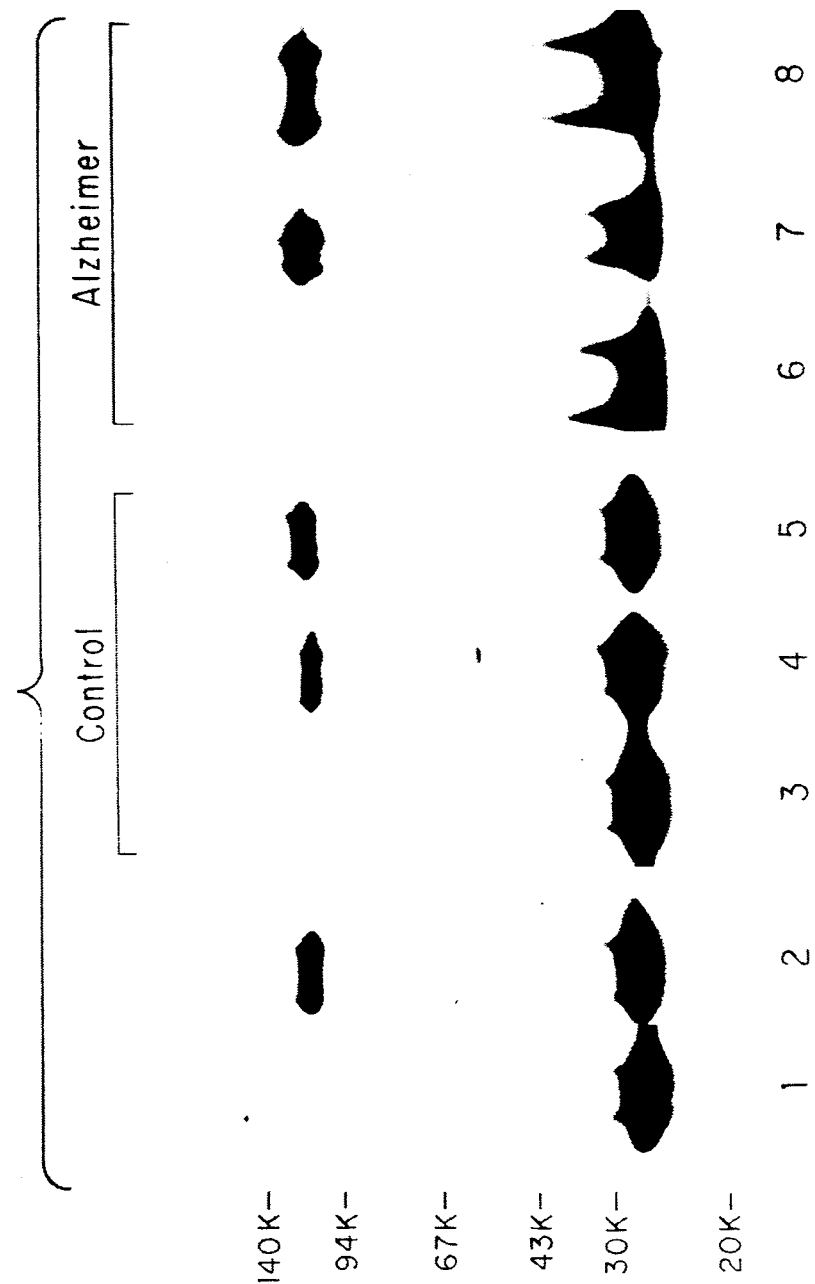

FIG. 6 is an autoradiogram showing $^{125}$I-EGF BP:PN-2/βAPP complex formation in platelet lysates.

FIG. 7, Panels A-D, shows Western blots of PN-2/βAPP in plasma and platelet lysates.

Figures 1, 8A:
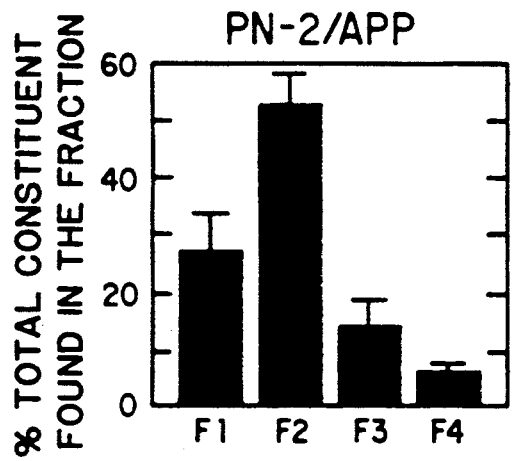
FIG. 1 shows the alignment of portions of the PN-2 and βAPP amino acid sequences, showing identity of PN-2 amino acid sequences within segments of the first 120 amino acids of the deduced βAPP sequence.
Figures 2, 8A:
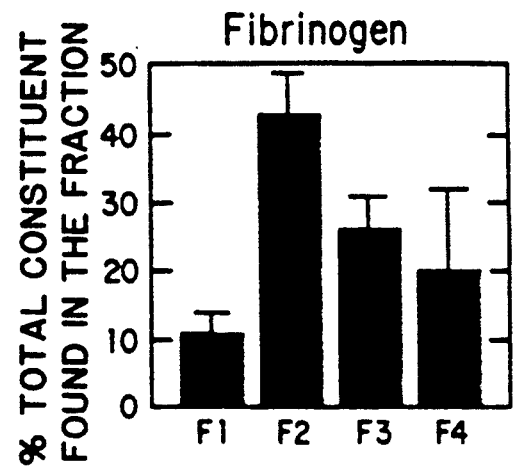
Figures 3, 8A:
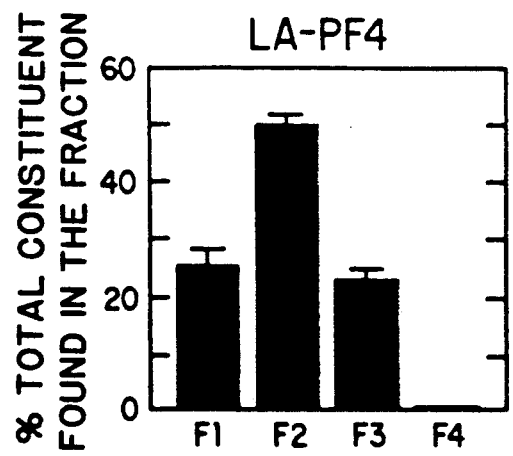
Figures 1, 8B:
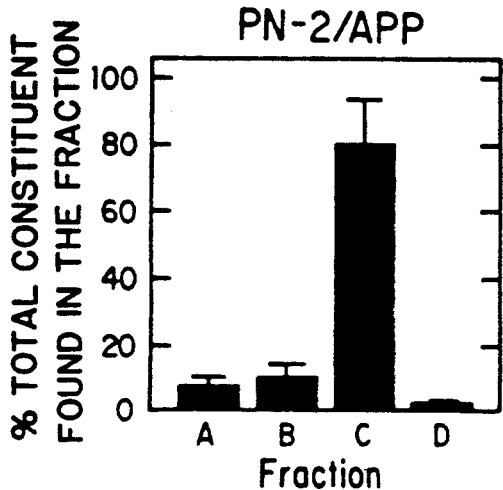
Figures 2, 8B:
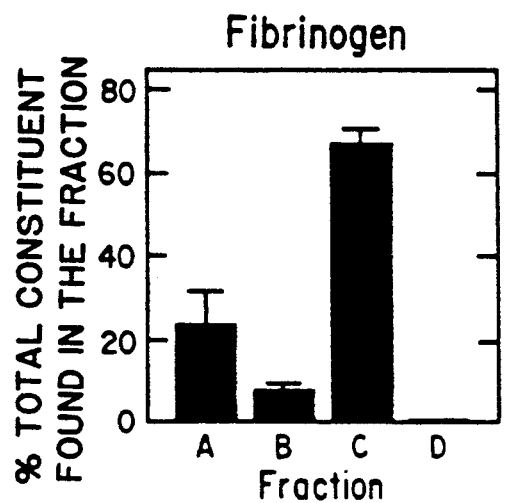
Figures 3, 8B:
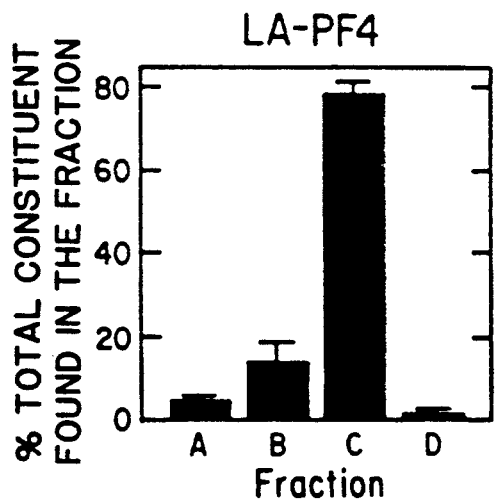
Figures 4, 8B:
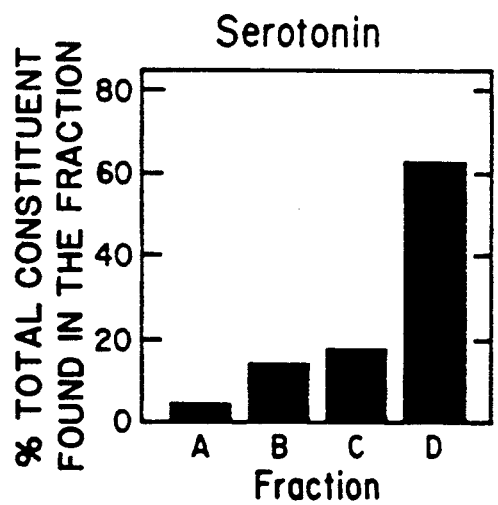

FIGS. 8a-8b show Platelet subcellular fractionation and localization of PN-2/βAPP.

Figure 9:
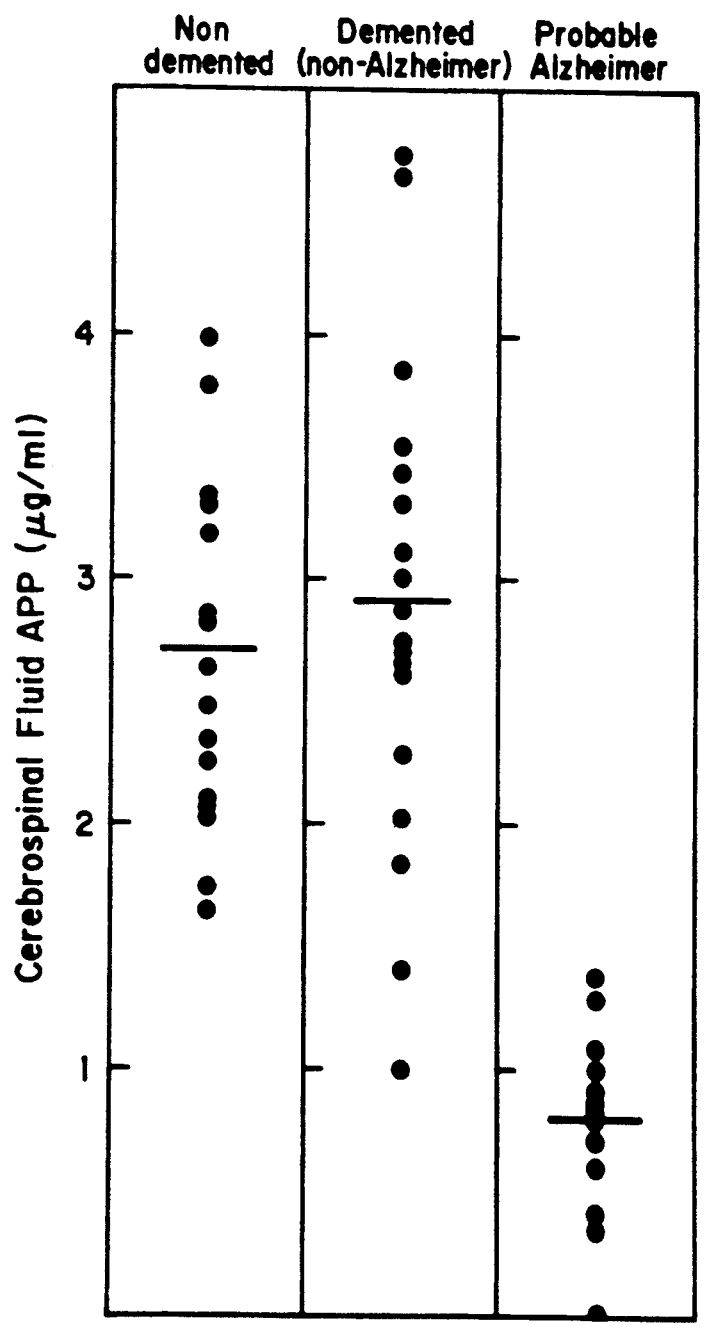

FIG. 9 shows Cerebrospinal Fluid Levels of PN-2/βAPP in 13 Patients Diagnosed with Probable Alzheimer's Disease, 18 Patients Diagnosed with Dementia (Non-Alzheimer Type), and 16 Non-Demented, Healthy Controls.

Figure 10A:
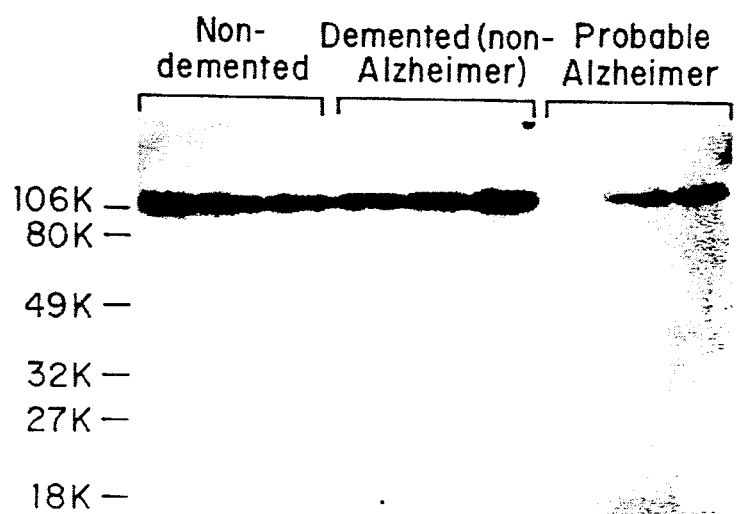
Figure 10B:
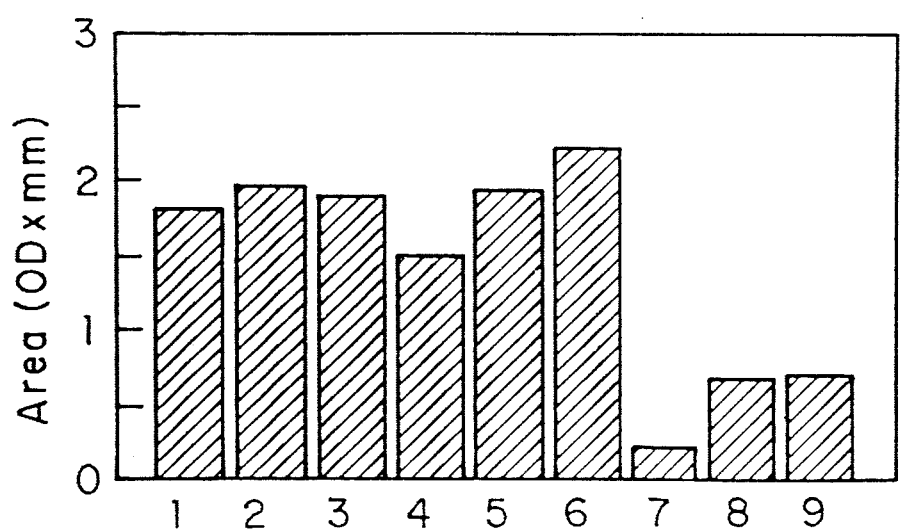

FIGS. 10A and 10B show an immunoblot analysis of PN-2/βAPP. FIG. 10A shows an immunoblot analysis of PN-2/βAPP in cerebrospinal fluid samples from 3 Non-Demented, Healthy Controls, 3 Patients Diagnosed with Dementia (Non-Alzheimer Type), and 3 Patients Diagnosed with Probable Alzheimer's Disease. The relative amount of immunoreactivity in each of the lanes of FIG. 10A, as measured by optical density scanning, is shown in FIG. 10B.

FIGS. 11A and 11B show the does relationship of PN-2/βAPP to mAbP2-1. FIG. 11A shows the dose relationship of ELISA assays performed using known quantities of PN-2/βAPP with mAbP2-1. FIG. 11B shows the results of ELISAs performed with known quantities of PN-2/βAPP in the absence of CSF (circles) and in the presence of control (squares) and AD CSF (triangles).

Figure 12A:
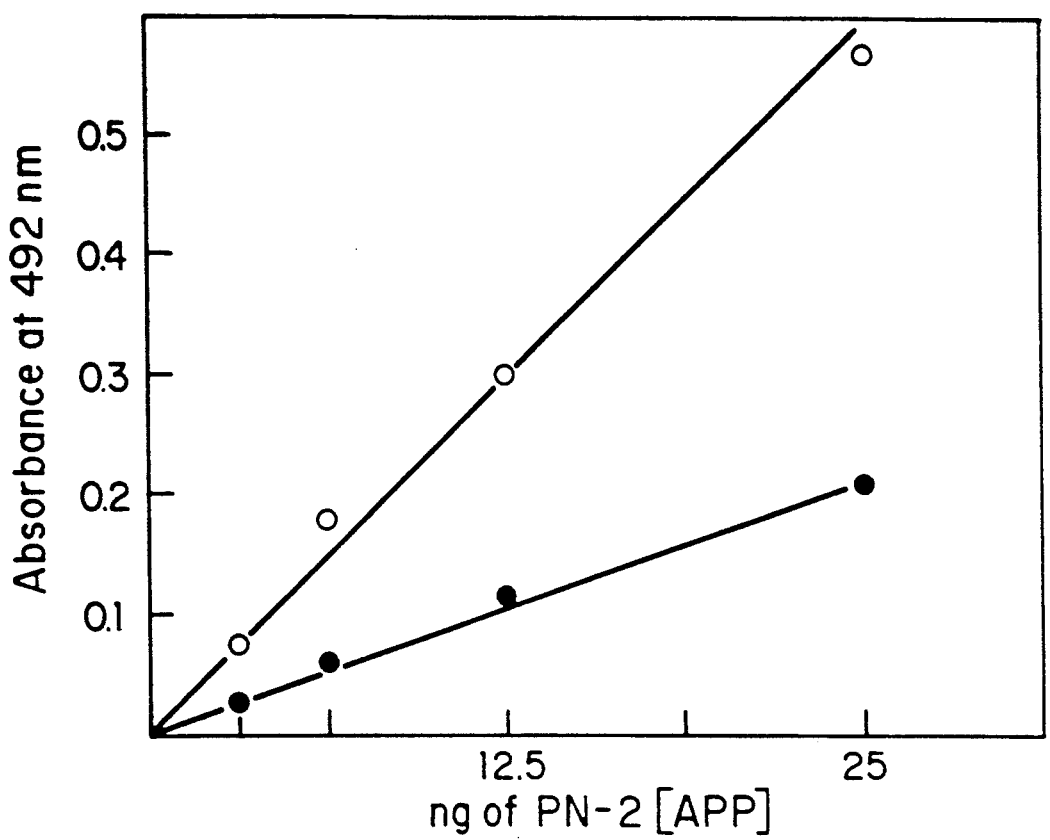
Figure 12B:
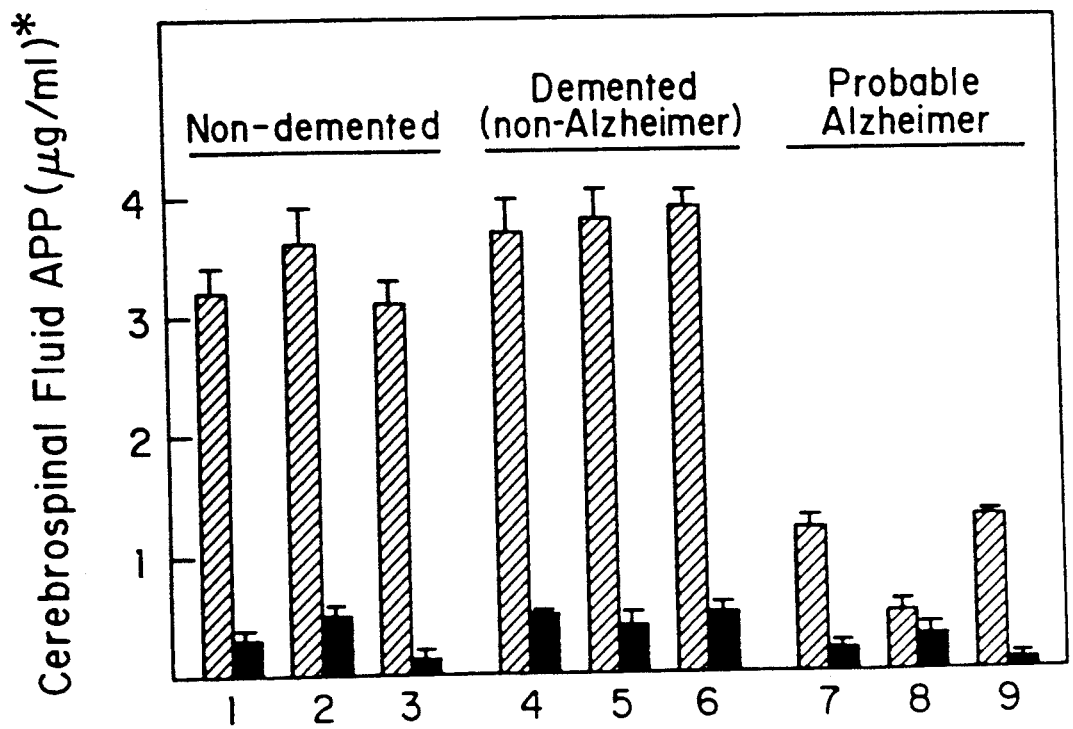

FIGS. 12A and 12B show the recognition of PN-2/βAPP by nAb22C11. FIG. 12A shows the dose-dependent recognition of PN-2/βAPP by mAb22C11 (shown with open circles) and mAbP2-1 (shown in darkened circles) in ELISA assays on known quantities of PN-2/βAPP. FIG. 12B shows ELISAs using both mAb22C11 and mAbP2-1 on CSF samples from non-demented, demented (non-Alzheimer type) and probable AD patients with results using mAb22C11 shown in solid bars and results using mAbP2-1 shown in striped bars.

Figure 13:

FIG. 13 shows the detection of hereditary cerebral hemorrhage with amyloidosis-Dutch type ("HCHWA-D") mutation in three patients using the single stranded conformation polymorphism technique in conjunction with polymerase chain reaction. Lanes 1-3 show the results for the HCHWA-D patients. Lane 4 shows results for a normal patient.

Figure 14A:
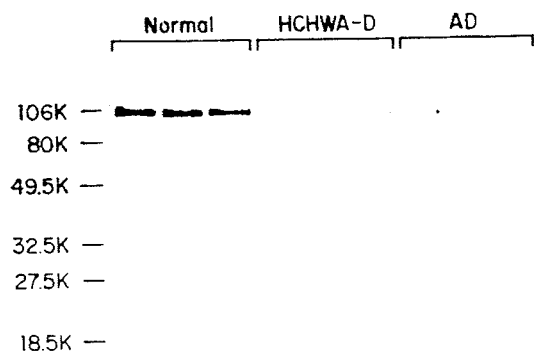
Figure 14B:
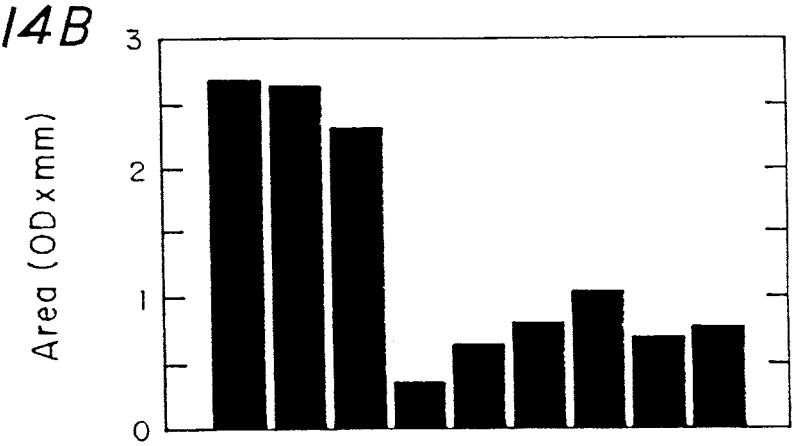
Figure 14C:
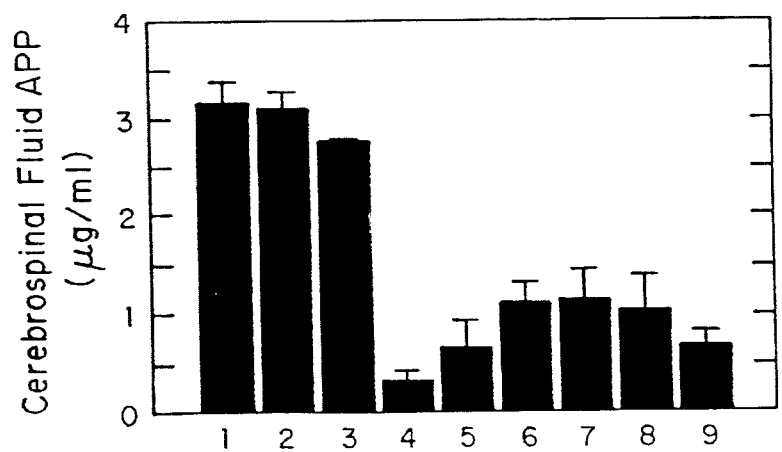

FIGS. 14a-c show an immunoblot and ELISA quantitation of PN-2/βAPP in CSF. (A) PN-2/βAPP was detected in aliquots of CSF from age-matched normals (lanes 1-3), HCHWA-D patients (lanes 4-6), and probable AD patients (lanes 7-9). (B) Quantitation of CSF PN-2/βAPP on immunoblots by scanning laser densitometry. (C) Quantitation of PN-2/βAPP by ELISA.

Figure 15:
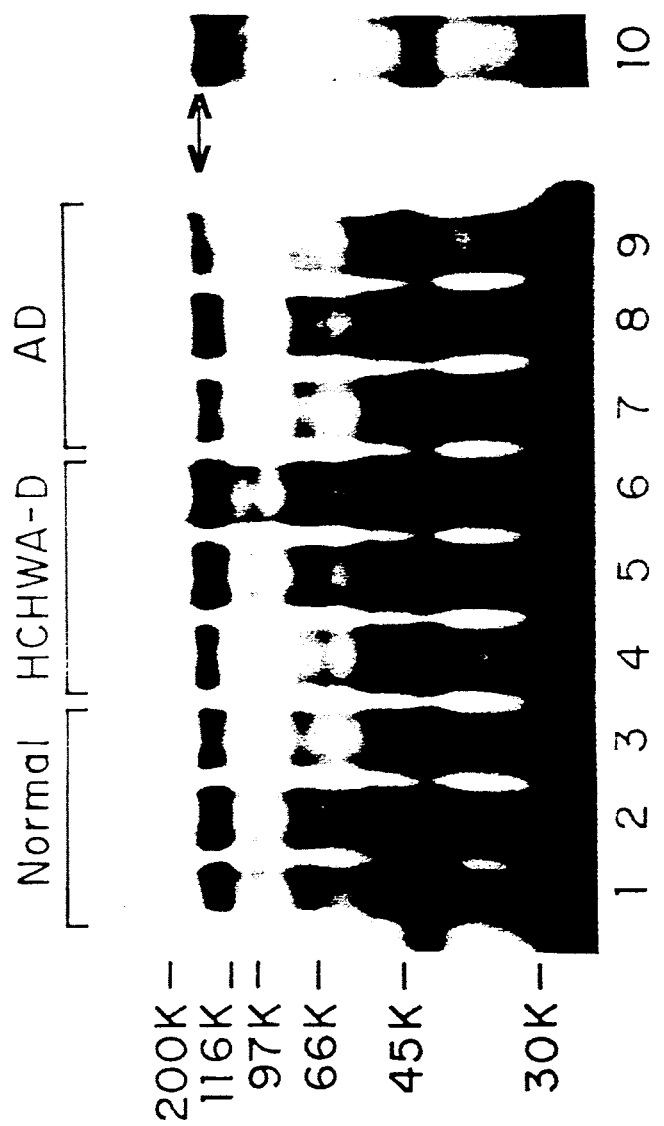

FIG. 15 shows an autoradiogram of radiolabeled protease:PN-2/βAPP complexes for the quantitation of KPI-Containing PN-2/βAPP in CSF samples: lanes 1-3 contained samples from age-matched normals, lanes 4-6 contained samples from HCHWA-D patients, lanes 7-9 contained samples from probable AD patients and lane 10 contained purified PN-2/βAPP. High molecular weight radiolabeled protease:PN-2/βAPP complexes are indicated by the arrows.

DETAILED DESCRIPTION OF THE PREFERRED EMBODIMENT

Immunopurification of PN-2

We have discovered the PN-2 specific monoclonal antibody producing hybridoma cell line mAbP2-1. We have further discovered an improved method for purifying PN-2 employing the monoclonal antibody produced by this cell line in an immunoaffinity step. In this method, we retained the primary dextran sulfate-Sepharose affinity step from our initial purification scheme reported in Van Nostrand, W. E., and Cunningham, D. D. J. Biol. Chem., 262: 8505-8514 (1987), the disclosure of which is hereby incorporated by reference. This step was retained because the step provides an effective means of concentrating the large volume of starting serum-free conditioned culture medium and enriches for PN-2.

The pooled PN-2-containing fractions from the primary dextran sulfate-Sepharose affinity step were then directly applied to a mAbP2-1 monoclonal antibody immunoaffinity column. After washing, apparently homogeneous PN-2 was eluted with low pH buffer. The overall activity yield from numerous purifications was between 70-85%. Importantly, only PN-2 can be detected with mAbP2-1 in the starting conditioned culture medium or pooled dextran sulfate-Sepharose fractions; further demonstrating its specificity, as well as sensitivity. The specificity of monoclonal antibody mAbP2-1 facilitated the purification of PN-2 from complex starting solutions such as tissue homogenates. The following examples describe the immunopurification and testing of purified PN-2.

EXAMPLE 1

Preparation of Column for Immunopurification of PN-2

Normal human neonatal foreskin fibroblasts were isolated from explants and cultured as previously described by Baker, J. B., et al., Cell, 21:37-45 (1980). Four liters of serum-free medium from microcarrier cultures of human fibroblasts were collected and chromatographed over a dextran sulfate-Sepharose affinity column.

The PN-2 specific monoclonal hybridoma cell line mAbP2-1, ATCC No. HB 10424, was prepared following procedures we described in Wagner, S. L. et al. Biochemistry 27:2173-2176 (1988), the disclosure of which is hereby incorporated by reference. Monoclonal antibody mAbP2-1 was purified from ascites fluid using an Affi-Gel Protein A MAPS Kit (BioRad Laboratories) and coupled to cyanogen bromide activated-Sepharose 4B (Pharmacia Biochemicals) as described by the manufacturer. A 4 ml column of mAbP2-1-Sepharose equilibrated with 20 mM potassium phosphate, 1 M NaCl, pH 7.4 was prepared.

EXAMPLE 2

Immunopurification of PN-2

PN-2-containing fractions from the dextran sulfate column were directly applied to the mAbP2-1-Sepharose column at a flow rate of 10 ml/h. After the column was loaded, it was washed with five column volumes of 20 mM potassium phosphate, 1 M NaCl, pH 7.4, followed by two column volumes of 20 mM potassium phosphate, 0.15 M NaCl, pH 7.4. The adsorbed PN-2 was eluted from the immunoaffinity column with 0.2 M glycine-HCl, 0.15 M NaCl, pH 2.8. 750 μl fractions were collected in tubes containing 75 μl of 2 M Tris-HCl, pH 8.3 to neutralize the elution buffer. During the purification, protein concentrations were determined by the method of Bradford, M. M., *Anal. Biochem.* 72: 680-685 (1976), the disclosure of which is hereby incorporated by reference.

EXAMPLE 3

PN-2 Activity Assay

In order to quantify the immunopurification of Example 2, known quantities of $^{125}$I-EGF BP were incubated with aliquots of samples containing PN-2 for 15 minutes at 37° C. An equal volume of SDS-PAGE sample buffer was added and the mixtures were subjected to SDS-PAGE. After autoradiography, PN-2 activity was monitored by the formation of a 120-kDa complex with the $^{125}$I-EGF BP. To quantitate PN-2 activity, the autoradiograms were aligned with the dried gels and the $^{125}$I-labeled complexes were located, excised and measured in a gamma counter. Units were expressed as pMoles of $^{125}$I-EGF BP complexed.

Table I shows the progressive purification after each column of the immunopurification procedure of Examples 1 and 2.

Sequence Analysis of PN-2

We have performed amino terminal amino acid sequence analysis on two peptides obtained from digestion of PN-2. The analysis revealed that PN-2 has sequence identity with at least portions of βAPP. The methods employed in this analysis are described in the following example.

EXAMPLE 4

Amino Acid Sequence Analysis of PN-2

Approximately 2 nmoles of purified PN-2 were digested with either CNBr or endoproteinase Lys-C (available from Boehringer Mannheim). The resulting peptides were subjected to SDS-polyacrylamide gel electrophoresis as described by Laemmli. The peptides were electroeluted from the gels onto Immobilon polyvinylidene difluoride membranes (available from Millipore) in a Transblot unit (available from BioRad Laboratories). After transfer, the membranes were stained with Coomassie Brilliant Blue R-250, destained and soaked in several changes of distilled water. A 12 kilodalton ("KD") CNBr peptide and a 20 KD endoproteinase Lys-C peptide were excised from the membranes and directly subjected to amino terminal amino acid sequence analysis using an Applied Biosystems 473-A Gas Phase Sequencer with an on-line microbore PTH-amino acid separator and data analyzer (available from Applied Biosystems in models 120-A and 900-A). The sequence determined is shown in FIG. 1.

The protein sequence database of the National Biomedical Research Foundation was searched with the PN-2 amino acid sequence data obtained from Example 4, and identity was found within the deduced sequence for the first 120 amino acids of βAPP. Accordingly, the deduced sequence for βAPP is shown in alignment with PN-2 sequences in FIG. 1.

As seen in FIG. 1, the amino terminus of PN-2 starts at position 18 of βAPP. Underlined PN-2 residues at positions 46-72 were derived from the PN-2 CNBr peptide. PN-2 residues at positions 46-50 of βAPP represent overlap from the amino terminal sequence of native PN-2 and the amino terminal sequence of the PN-2 CNBr peptide. The arrow at position 44 represents an uncertain phenylalanine from the original amino terminal sequence of native PN-2 and is the only discrepancy in the alignments. Underlined PN-2 residues at positions 107-116 were derived from a PN-2 endoproteinase Lys-C peptide. No determination could be made for position 108 of PN-2.

Identity of PN-2 and βAPP

FIG. 1 reveals that the only discrepancy between sequenced regions of PN-2 and corresponding segments of βAPP was at amino acid residue 27 of PN-2. The βAPP cDNA predicts a histidine residue at the position corresponding to position 27 of PN-2, which we reported as a questionable phenylalanine. Based on the observed sequence identity along with reports that certain forms of βAPP possesses a proteinase inhibitory domain and proteinase inhibitory activity, we believe that PN-2 and a secreted form of βAPP containing the Kunitz inhibitor domain are the same or very similar proteins.

Cultured human glioblastoma cells and neuroblastoma cells have been shown to express mRNA for βAPP and to secrete the protein. βAPP mRNA and protein have also been detected in human brain. To further confirm our belief that PN-2 and βAPP were the same or similar proteins, immunoblot analysis for PN-2 was performed using these cell lines, as in the following example.

EXAMPLE 5

Immunoblot Analysis of PN-2

A PN-2-specific monoclonal hybridoma cell line was prepared as discussed in Example 1. Normal human neonatal foreskin fibroblasts, human glioblastoma HTB-14 and human neuroblastoma HTB-11 cells were cultured in Dulbecco's Modified Eagle Medium containing 10% fetal bovine serum and antibiotics. Serum-free medium from the cultured cells was concentrated and enriched for PN-2 by passing 100 ml of medium through a 1 ml DEAE-Sepharose column; the adsorbed protein was eluted with 2 ml of 1 M NaCl. Human brain parietal cortex sections were placed in a buffer (20 ml/gm tissue) containing 200 mM NaCl, 20% glycerol, 1% Triton X-100 and 20 mM potassium phosphate, pH 7.4, homogenized for 5 minutes using a Polytron and centrifuged at 10,000 x g for 15 minutes at 4° C. to remove particulates. For immunoblots, samples were subjected to SDS-PAGE; completed gels were soaked in transfer buffer and the proteins were electroeluted onto Immobilon polyvinylidene difluoride membranes for 2.5 hours at 0.4A in a Transblot unit. The membranes were gently agitated in TBS (50 mM Tris-HCl, 150 mM NaCl, pH 7.5) containing 0.25% gelatin overnight at 25° C. to block unoccupied sites followed by incubation with mouse monoclonal mAbP2-1 hybridoma culture supernatant for 1 hour at 37° C. with gentle agitation. After several washes with TBS containing 0.05% Tween-20, bound mouse mAbP2-1 was detected with a biotinylated-sheep anti-mouse IgG (Amersham) and a streptavidin-horseradish peroxidase complex with several washes between each step. To develop the immunoblots, 48 mg of 4-chloronapthol were dissolved in 16 ml of ice-cold methanol and this was added to 80 ml of ice-cold TBS followed by the addition of 64 μl of $H_2O_2$. The developed immunoblots are shown in FIG. 2a.

Figure 2A:
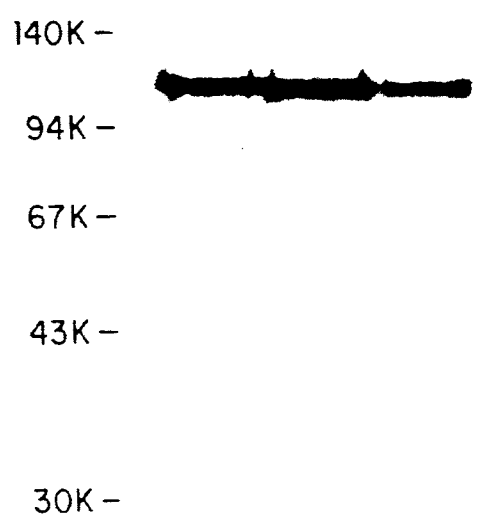
FIGS. 2a and 2b show immunoblot analysis of PN-2 in cell culture media and brain tissue homogenates. a, Monoclonal antibody mAbP2-1 stained identical proteins in PN-2-enriched culture medium from normal human fibroblasts (lane 1), human glioblastoma cells (lane 2) and human neuroblastoma cells (lane 3). b, This same monoclonal antibody stained apparently identical proteins in tissue homogenates from normal (lane 1) and Alzheimer's disease (lane 2) brain.

The immunoblots of FIG. 2a show that the PN-2-specific monoclonal antibody mAbP2-1 recognized a protein in the culture medium of glioblastoma cells (lane 2) and neuroblastoma cells (lane 3), cells known to secrete βAPP. Moreover, it can be seen that the protein recognized in both of these cell cultures co-migrated in SDS-PAGE with the PN-2 present in human fibroblast culture medium (lane 1). Thus, Example 5 provides further support for our belief that the secreted form of βAPP containing the Kunitz inhibitor domain and PN-2 are the same or very similar proteins.

In view of the findings from Example 5, the term "PN-2/βAPP" is used herein to refer to the various forms of these proteins jointly. However, PN-2 and βAPP are not equivalent terms, and where appropriate, the particular form of these related proteins is distinguished herein through use of the terms separately. Thus, as described above, "PN-2" is used herein to refer to the "correctly" processed, secreted form of the 751 amino acid Kunitz protease inhibitory (KPI) domain containing form of βAPP, and "$APP_{695sec}$" refers to the "correctly" processed, secreted form of the 695 amino acid non-KPI-containing form of βAPP. PN-2 and $APP_{695sec}$ represent the two most abundant forms of PN-2/βAPP present in human tissue. The processing which is referred to by use of the term "'correctly' processed" is the processing which results in the formation of these two abundant secreted forms of PN-2/βAPP in normal individuals.

Use of mAbP2-1 in the Diagnosis of Alzheimer's

Figure 2B:
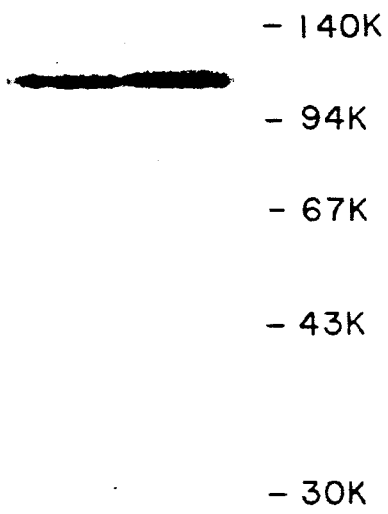

We also used mAbP2-1 in immunoblots of tissue homogenates of the parietal cortex of healthy brain and of Alzheimer's disease brain. FIG. 2b shows these results; lane 1 is a blot of SDS-PAGE of parietal cortex homogenate of healthy brain and lane 2 of Alzheimer's brain. As can be seen in FIG. 2b, MAbP2-1 recognized a protein in tissue homogenates prepared from the parietal cortex of both healthy brain or Alzheimer's disease brain. Thus, the mere finding PN-2 immunoreactivity in brain tissue homogenates does not serve as an indication of Alzheimer's. However, immunostaining with mAbP2-1 will selectively stain neuritic plaques in tissue sections of Alzheimer's disease brain.

Thus, we have discovered that mAbP2-1 can be effectively used to diagnose Alzheimer's at autopsy. The following example shows a typical method for immunostaining brain tissue to reveal the presence of PN-2 immunoreactivity in Alzheimer's disease brain.

EXAMPLE 6

Immunostaining of Alzheimer's Disease Brain

Tissues were fixed overnight in 2% paraformaldehyde and 0.01% glutaraldehyde. After washing in phosphate buffered saline ("PBS"), vibratome sections were prepared and subsequently processed using a avidin-biotin complex immunoperoxidase detection system for PN-2 which uses the PN-2-specific antibody mAbP2-1. Results are seen in FIG. 3.

Figure 3A:
FIGS. 3a and 3b show immunostaining of Alzheimer's disease neuritic plaques with monoclonal antibody mAbP2-1. a, Photomicrograph showing strong immunoperoxidase reaction for PN-2 in scattered neuritic plaques (open arrows) within the CA1 region of the hippocampus of a 62-year-old female patient with Alzheimer's disease. Solid arrow points to a pyramidal neuron Vibratome section (40 µm) viewed by bright field microscopy. X200. b, Photomicrograph of a neuritic plaque on higher magnification showing strong immunoperoxidase reaction for PN-2 (open arrow)
Figure 3B:

FIG. 3a shows that mAbP2-1 exhibited intense staining of neuritic plaques with the CA1 region of the hippocampus of a patient with Alzheimer's disease. Staining was not observed in age-matched controls (data not shown). Higher magnification of a neuritic plaque, seen in FIG. 3b, showed that the staining was more pronounced at the periphery.

Thus, Example 6 illustrates one method of diagnosing Alzheimer's at autopsy by the specific immunostaining of neuritic plaques with mAbP2-1.

Physiological Function for PN-2/βAPP

Several considerations suggest that one physiological function for PN-2/βAPP is the regulation of a chymotrypsin-like proteinase. One such consideration is derived from the finding that neuritic plaques in Alzheimer's disease contain A4 which is cleaved from βAPP by proteolytic cleavage. Studies have shown that βAPP can be translated from at least three alternatively spliced mRNAs, only two of which contain an insert encoding for a Kunitz-type protease inhibitor domain. Alzheimer's patients have been found to have an excess of mRNA coding for βAPP lacking the Kunitz-type proteinase inhibitor domain. Thus, we believe that this proteinase inhibitor domain is critical in preventing the build-up of A4 in neuritic plaques.

Another consideration is that it has been reported that a methionine residue flanks the amino terminal side of the peptide bond that is cleaved upon release of A4 from βAPP. This site is susceptible to cleavage by a chymotrypsin-like proteinase to release the A4 protein. Accordingly, we believe that one physiological function of PN-2/βAPP is the inhibition of this chymotrypsin-like proteinase.

We tested the ability of purified PN-2 to inhibit a variety of serine proteinases employing spectrophotometric assays with chromogenic substrates. We found that PN-2 was a potent inhibitor of chymotrypsin. Although the formation of complexes between chymotrypsin and PN-2 was not observed by SDS-PAGE, stable chymotrypsin-PN-2 binding was identified with a $^{125}I$-chymotrypsin blotting assay. The following is an example of such an assay.

EXAMPLE 7

$^{125}I$-Chymotrypsin Blotting Assay

Two μg of purified PN-2 were subjected to SDS-PAGE. The complete gel was soaked for 10 minutes in a transfer buffer consisting of 10 mM sodium bicarbonate, 3mM sodium carbonate, 20% methanol, pH 9.9 and the PN-2 was electroeluted onto a nitrocellulose membrane for 2 hours at 400 mA in Transblot unit (available from BioRad Laboratories). After transfer, the nitrocellulose membrane was gently agitated overnight in a solution of TBS containing 0.25% gelatin to block unoccupied sites on the membrane and then incubated with a solution of TBS containing 20 ng/ml of $^{125}I$- chymotrypsin (specific activity=$5.5 \times 10^5$ cpm/pmole) for 20 minutes at 25° C. followed by two 10 minutes washes with TBS containing 0.05% Tween-20 and a final wash in TBS. Membranes were dried and exposed to X-ray film for 12 hours at −70° C. The resulting autoradiogram is shown in FIG. 4. The autoradiogram demonstrates that $^{125}$I-chymotrypsin bound to purified PN-2 that had been transferred to a nitrocellulose membrane after SDS-PAGE. A similar assay showed that $^{125}$I-chymotrypsin bound to PN-2 after SDS-PAGE of brain tissue homogenates and cell culture media from neuroblastoma and glioblastoma cells (data not shown).

To further examine the inhibition of chymotrypsin by PN-2 the inhibition equilibrium constant ($K_i$) was measured for the reaction. These studies revealed that PN-2 was a potent and reversible inhibitor of chymotrypsin with a $K_i = 6 \times 10^{-10}$ M. Reversible inhibition is characteristic of the Kunitz-type serine proteinase inhibitors which are homologous to a domain in $\beta APP_{751}$. Incubation of PN-2 with chymotrypsin resulted in proteolytically processed forms of PN-2 which still retained their ability to bind and inhibit chymotrypsin (data not shown). These results are similar to results reported for another Kunitz-type inhibitor, plasma inter-$\alpha$-trypsin inhibitor. Thus, we concluded that, like $\beta APP_{751}$, PN-2 has Kunitz-type inhibitor activity. To further test this conclusion, we performed further proteinase inhibition studies of the purified PN-2 from Example 2 on a variety of proteinases. The following example shows one such study in which PN-2 was found to be an effective inhibitor of both chymotrypsin-like and trypsin-like proteases.

EXAMPLE 8

Proteinase-Blot Analysis of PN-2/$\beta$APP

Aliquots of purified PN-2/$\beta$APP were subjected to 10% SDS-PAGE and completed gels were soaked in transfer buffer (10 mM sodium bicarbonate, 3 mM sodium carbonate, 20% methanol, pH 9.9) for 10 minutes. The proteins were electroeluted from the gels onto nitrocellulose membranes for 2.5 hours at 0.4 A in a Transblot apparatus and then gently agitated in TBS containing 0.25% gelatin overnight at 25 C to block unoccupied sites. The nitrocellulose membranes were then incubated with $^{125}$I-protease (20-50 ng/ml) for 30 minutes at 25° C. followed by two 10 minutes washes with TBS containing 0.05% Tween-20 and a final wash in TBS. Membranes were then air dried and exposed to X-ray film for 12-24 hours at −70° C. Results are shown in FIGS. 5(a) and 5(b) and reported in Table II.

FIG. 5(a) shows that the low molecular weight "trypsin-like" proteases including EGF BP (lane 2), NGF-$\gamma$ (lane 4) and trypsin (lane 6) formed SDS-stable complexes with PN-2/$\beta$APP. In contrast, neither the higher molecular weight "trypsin-like" proteases factor XIa and plasmin nor "chymotrypsin-like" proteases chymotrypsin and chymase formed SDS-stable complexes with PN-2/$\beta$APP (data not shown). We employed the protease blotting technique of Example 8 to demonstrate stable binding of this group of proteases to PN-2/$\beta$APP.

FIG. 5(b) shows that $^{125}$I-labeled proteases bound to PN-2/$\beta$APP that was immobilized on nitrocellulose. Thus Example 8 shows that a spectrum of different stabilities exist for complexes between PN-2/$\beta$APP and the proteases it inhibits. Although complexes between certain proteases and PN-2/$\beta$APP are stable in SDS-PAGE without prior boiling, the kinetic studies indicate that these complexes are indeed reversible.

Table II lists the inhibition equilibrium constants ($K_i$) obtained in Example 8 for PN-2/$\beta$APP with a variety of serine proteases. PN-2/$\beta$APP was a potent inhibitor of the blood coagulation protease factor XIa. The finding that heparin enhanced the inhibition of factor XIa by PN-2/$\beta$APP suggests that the other domains (i.e., heparin binding domains) may be important in the inhibition of certain target proteases. In addition, PN-2/$\beta$APP effectively inhibited trypsin, chymotrypsin and two closely related serine proteases obtained from mouse submandibular gland, EGF BP and NGF-$\gamma$. Chymase and plasmin were inhibited to a lesser extent. PN-2/$\beta$APP did not significantly inhibit plasminogen activators, tissue kallikrein, pancreatic elastase or several other proteases from the coagulation pathway.

The finding that PN-2/$\beta$APP can inhibit serine proteases of two different class specificities is noteworthy. Factor XIa, trypsin, EGF BP, NGF-$\gamma$ and plasmin are all "trypsin-like" in specificity in that they cleave peptide bonds on the carboxyl side of the basic amino acids lysine or arginine. In contrast, chymotrypsin and chymase preferentially cleave peptide bonds on the carboxyl side of large side chain amino acids. The deduced amino acid sequence of PN-2/$\beta$APP aligned with other Kunitz-type serine protease inhibitors predicts $Arg^{301}$ to reside in the P1 site of the reactive center. This is consistent with the inhibition of the "trypsin-like" proteases factor XIa, trypsin, EGF BP, NGF-$\gamma$ and plasmin. In several instances strong inhibitors of trypsin with a $P_1$ Arg or Lys inhibit chymotrypsin at the same site. A similar mechanism may occur for inhibition of chymotrypsin and chymase by PN-2/$\beta$APP. Alternatively, another site may be responsible for the inhibition of "chymotrypsin-like" proteases.

A recent study by Potempa, et al., *Science*, 241:6-99-700 (1988), the disclosure of which is hereby incorporated by reference, showed that $\alpha_2$-antiplasmin can inhibit "trypsin-like" plasmin at the $Arg^{364}$-$Met^{365}$ bond or chymotrypsin at the adjacent $Met^{365}$-$Ser^{366}$ bond. It is possible that an adjacent site in PN-2/$\beta$APP may be responsible for the "chymotrypsin-like" inhibition. We found that preformed EGF BP-PN-2/$\beta$APP complexes did not inhibit chymotrypsin (data not shown) consistent with the possibility of identical or adjacent inhibitory sites. Alternatively, formation of EGF BP-PN-2/$\beta$APP complexes may induce a conformational change in PN-2/$\beta$APP that renders it inactive towards inhibiting of chymotrypsin.

Our discoveries that PN-2 is the same or very similar protein as $\beta APP_{751}$ and that PN-2 has a Kunitz-type inhibitor domain led us to a further discovery that PN-2 is useful in inhibiting the altered extracellular proteolysis implicated in Alzheimer's disease.

Thus, one aspect of the invention involves administration of PN-2 to a mammal to inhibit deposition of A4 in neuritic plaques. In this regard, we believe that administration of PN-2 in sufficient amounts to inhibit cleavage of PN-2 to release A4 is effective in inhibiting the deposition of neuritic plaques. Neuritic plaques are implicated in Alzheimer's, Down's, and possibly other diseases. Thus, we believe that administration of effective plaque-deposition-inhibiting amounts of PN-2 are effective in the treatment and prevention of these diseases.

We believe that a therapeutically effective amount of PN-2 is that which will raise levels of PN-2/$\beta$APP in the CSF to near normal or above-normal levels. As described hereinbelow, in connection with Tables IV and V, we have discovered that normal levels of PN-2/βAPP in the CSF are at approximately 3 µg/ml. Accordingly, we believe that therapeutic dosages of PN-2 will provide CSF levels of PN-2/βAPP within the range 1 µg/ml to 100 µg/ml, and more preferably in the range 3 µg/ml to 10 µg/ml.

Accordingly, in certain preferred embodiments of the present invention, PN-2 is formulated into pharmaceutical preparations. These pharmaceutical preparations may further include other pharmaceutically active ingredients. In addition, any of the well-known pharmaceutically acceptable carriers or excipients may be combined with PN-2 in well-known manner. Administration may be intramuscular, intravenous, intraperitoneal, or by any other method suitable for delivering active pharmaceuticals to the body and to the brain.

Example 9 shows an exemplary therapeutic composition for administering PN-2 to a patient.

EXAMPLE 9

An Injectable Composition for Prevention of Alzheimer's 2 mg/ml: PN-2
balance: sterile $H_2O$ Therapeutic dosages of PN-2 when used for intravenous injections in accordance with a method of the preferred embodiment are, preferably, the amount required to provide a level of PN-2/βAPP in the CSF in the patient of 3 µg/ml to 10 µg/ml. Levels of PN-2/βAPP can be assayed by the method of Example 20 described below. The levels of PN-2/βAPP in the CSF can also be measured quantitatively using the monoclonal antibody of the present invention in either a quantitative Western Blot or by an ELISA assay. Example 10 illustrates one immunological method of quantitating the level of PN-2/βAPP in CSF used in order to determine appropriate therapeutic dosages of PN-2.

EXAMPLE 10

Western Blot for PN-2/βAPP in Human CSF

Human CSF is obtained from a healthy human subject and subjected to SDS-PAGE. Standards having known amounts of PN-2/βAPP are also run on the gels. The resulting gels are transferred to nitrocellulose membranes and exposed to $^{125}I$ labeled mAbP2-1. The membranes are exposed to film and the resulting autoradiograms are analyzed for the presence of PN-2/βAPP immunoreactivity using a scanner instrument. The CSF values are compared with those for the known standards to make a quantitative determination of the amount of PN-2/βAPP in the CSF samples.

When using the pharmaceutical compositions of Example 9, the dose will depend on the level of PN-2/βAPP in the CSF of the patient. Thus, in the treatment of these patients, the CSF level of PN-2/βAPP immunoreactivity may be periodically monitored to keep the levels of PN-2/βAPP within the preferred therapeutic range. Example 11 illustrates a preferred method of the present invention of preventing Alzheimer's disease in a susceptible patient.

EXAMPLE 11

Prevention of Alzheimer's Disease with PN-2

Five patients with very early stage Alzheimer's disease receive 1.0 cc of the composition of Example 9 intracranially once per day. A matched control group of five patients receive an equal amount of the composition of Example 9 without any active ingredient. The treatments are continued every day for a period of five years. Once per week for the first month, and once every three months thereafter, the level of PN-2/βAPP in each patient's CSF from the PN-2 group is monitored by the method of Example 10. The dosage is adjusted to keep the level of PN-2/βAPP in the patient's CSF within the range of 3 µg/ml to 10 µg/ml. At the end of five years, the PN-2/βAPP group is functioning well with little or no reduction in levels of ability to care for themselves or in memory. The control group exhibits significantly deteriorated memory and ability to care for themselves.

The foregoing examples show the utility of native PN-2 in effectively preventing further neurodegeneration associated with Alzheimer's. It is believed that administration of PN-2 in the manner of Example 11 will prevent any further neurodegeneration associated with Down's syndrome and other diseases as well. However, still greater effectiveness is believed obtainable from PN-2/βAPP which has been modified by deletion of some or all of the A4 region of native PN-2/βAPP. This is because native PN-2 not only provides the protease inhibiting domain but also provides at least a portion of the A4 region itself.

Recent data suggest that PN-2 contains at least some of the A4 region. It is not known which, if any, of the normal PN-2/βAPP proteins contain all of the A4 region. One theory is that normal, unprocessed βAPP contains only a portion of the A4 region and that incorrectly processed βAPP in Alzheimer's patients may have the entire A4 domain. However, a competing theory is that both normal and Alzheimer's βAPP contain the entire A4 domain, but that the A4 protein is cleaved from Alzheimer's βAPP as the protein is extruded through cell membranes to produce PN-2, and $APP_{695sec}$ and incorrectly processed forms of βAPP.

If the latter theory is correct, then it is believed that addition of PN-2 to a patient may have the unintended effect of providing more substrate for the release of A4. Thus, we believe that PN-2/βAPP lacking some or all of the A4 region may prove more effective in inhibiting deposition of neuritic plaques in a mammal.

Example 12 shows an exemplary method of obtaining a modified PN-2/βAPP containing the entire Kunitz inhibitory domain and lacking all of A4.

EXAMPLE 12

Cloning and Expression of Modified PN-2/βAPP Lacking a Portion of the A4 Region

A cDNA plasmid containing the gene for native PN-2/βAPP containing the Kunitz protease inhibitory domain is obtained and the cDNA containing the native sequence is excised. A unique restriction site between the region coding for the Kunitz inhibitor domain and the A4 domain is located. The appropriate restriction enzyme is applied and the fragment containing the Kunitz inhibitor domain is isolated. A vector is chosen for expression of cloned sequences in yeast. Appropriate linker fragments are added to the Kunitz inhibitor domain containing fragment and the fragment is inserted into the vector. Expression in yeast produces the modified PN-2/βAPP.

Thus, Example 12 shows an exemplary method of cloning and expressing modified PN-2/βAPP. A similar method without the modification to the PN-2/βAPP gene can be employed to clone and express native PN-2/βAPP. As an alternative to the cloning and expression of modified PN-2/βAPP, it may be possible to cleave and isolate the Kunitz domain from PN-2/βAPP. This isolated protein fragment is expected to prove effective in preventing the deposition of amyloid plaques.

EXAMPLE 13

A Modified Composition Effective in Inhibiting Deposition of Neuritic Plaques 2 mg/ml: modified PN-2/βAPP from Example 12
balance: sterile $H_2O$

EXAMPLE 14

Prevention of Alzheimer's Disease

Five patients with very early stage Alzheimer's disease receive 1.0 cc of the composition of Example 13 intracranially once per day. A matched control group of five patients receive an equal amount of the composition of Example 13 without any active ingredient. The treatments are continued every day for a period of five years. At the end of five years, the PN-2/βAPP group is functioning well with no reduction in levels of ability to care for themselves or in memory. The control group exhibits significantly deteriorated memory and ability to care for themselves.

Circulating Source of PN-2/βAPP

Deposition of A4 at sites of cerebrovascular malformations led us and others to conclude that abnormalities of blood vessel walls might lead to its deposition from the circulation. In addition, a recent report showed evidence for the deposition of A4 in non-neural tissues in Alzheimer's disease which also suggested the likelihood of a circulating source of A4. However, heretofore evidence for a plasma source of PN-2/βAPP or A4 has been lacking.

We have discovered the major circulating source of PN-2/βAPP by screening different fractions of whole blood employing functional and immunochemical assays. The functional assay was based on the ability of PN-2/βAPP to form SDS-stable complexes with EGF BP that can be detected after electrophoresis.

We looked for PN-2/βAPP in fractionated plasma and in platelet lysates prepared from fresh blood of a control and Alzheimer's disease patient. The functional assay we performed involved incubating the blood fractions with $^{125}I$ labeled EGF BP in order to allow complexes of PN-2/βAPP:EGF BP to form. SDS-PAGE was run and the complexes were detected as high molecular weight labeled bands. We could not detect PN-2/βAPP:EGF BP in the assays we performed on plasma. However, these complexes were detected in assays performed on platelet lysates taken from the same patients.

Before assaying the plasma, it was first fractionated over a DEAE-Sepharose anion exchange column to concentrate and enrich for PN-2/βAPP, as in Example 1. This step also removed the large amounts of albumin, immunoglobulins and other endogenous protease inhibitors. The following example shows a typical assay for PN-2/βAPP in platelet and plasma fractions.

EXAMPLE 15

PN-2/βAPP:EGF BP Complex Formation

Platelet poor plasma and platelets were prepared from freshly collected blood obtained from control and diagnosed Alzheimer's disease patients. Ten ml aliquots of plasma were diluted with 20 ml of 20 mM potassium phosphate, 0.2 M NaCl, pH 7.4. As a control, purified PN-2/βAPP was added to some plasma aliquots at a final concentration of 0.5 nM. All plasma samples were then passed through 1 ml DEAE-Sepharose columns, the columns were then washed with 25 ml of the above buffer. Adsorbed proteins were eluted from the columns with 20mM potassium phosphate, 1 M NaCl, pH 7.4. Platelets were resuspended to a final concentration of 0.5 to $1.0 \times 10^9$/ml and solubilized by incubation with 0.5% Triton X-100 for 30 minutes at room temperature. Aliquots of the DEAE-Sepharose eluates and platelet lysates were then incubated with 40 ng of $^{125}I$-EGF BP ($1.75 \times 10^6$ cpm/pmole) for 15 minutes at 37° C. An equal volume of SDS-sample buffer was added and the samples were subjected to nonreducing 10% SDS-PAGE. Completed gels were dried and autoradiograms were prepared.

The autoradiogram from Example 15 is shown in FIG. 6. Lane 1 was $^{125}I$-EGF BP alone; lane 2 was $^{125}I$-EGF BP+purified PN-2/βAPP; lanes 3 and 6 were $^{125}I$-EGF BP+plasma; lanes 4 and 7 were $^{125}I$-EGF BP+platelet lysates; and lanes 5 and 8 were $^{125}I$-EGF BP+Plasma+purified PN-2/βAPP (0.5 nM). Lanes 5 and 8 were run to clearly show that purified PN-2/βAPP in an equivalent amount of plasma and followed by the same fractionation procedure would be detected by this assay.

We also ran Western blots of gels of fractionated blood components. These assays showed the absence of PN-2/βAPP immunoreactivity in the fractionated plasma samples using the anti-PN-2/βAPP mouse monoclonal antibody mAbP2-1, described in Example 1, or affinity purified anti-PN-2/βAPP rabbit polyclonal IgG. In these experiments the plasma was fractionated as described above for the functional assays. Western blotting of unfractionated plasma samples also failed to reveal immunoreactivity for PN-2/βAPP or fragments of it (data not shown). In contrast, both anti-PN-2/βAPP antibodies clearly recognized PN-2/βAPP in the platelet lysates. The following are examples of these Western Blot assays we performed to further show that circulating PN-2/βAPP was localized to platelet fractions.

EXAMPLE 16

Western Blot for PN-2/βAPP using mAbP2-1

Samples of plasma and platelets from control and Alzheimer's disease patients were prepared as described in Example 15. Samples were subjected to 10% SDS-PAGE followed by electro-elution onto nitrocellulose membranes for 2.5 hours at 0.4 A in a Transblot unit (BioRad Laboratories). The membranes were gently agitated overnight at 25° C. in TBS (50mM Tris-HCl, 150 mM NaCl, pH 7.5) containing 0.25% gelatin to block unoccupied sites, and then incubated with mouse monoclonal mAbP2-1 hybridoma culture supernatant for 1 hour at 37° C. with gentle agitation. After several washes with TBS containing 0.05% Tween-20, bound mouse mAbP2-1 was detected with a biotinylated sheep anti-mouse IgG (Amersham) and a streptavidin-horseradish peroxidase complex. To develop the Western blots, 48 mg of 4 chloronapthol were dissolved in 16 ml of ice-cold methanol which was added to 80 ml of ice-cold TBS, followed by addition of 64 µl of $H_2O_2$. Results are shown in FIG. 7, panel A. Lane 1 was purified human fibroblast PN-2/βAPP; lane 2 was fractionated plasma from a healthy patient; lane 3 was platelet lysate from a healthy patient; lane 4 was fractionated plasma from an Alzheimer's patient; and lane 5 was platelet lysate from an Alzheimer's patient. These results clearly show that immunoreactivity in blood towards mAbP2-1 was found only in platelets of both healthy and Alzheimer's patients.

EXAMPLE 17

Western Blot for PN-2/βAPP using polyclonal IgG

Western blots were performed as described in Example 16 except that affinity purified rabbit polyclonal IgG was used as the primary antibody. Bound rabbit antibody was detected using a biotinylated donkey anti-rabbit IgG (Amersham) and a streptavidin-horseradish peroxidase complex. Results are shown in FIG. 7, Panel B, with lane designations as in Example 16. These results also show that PN-2/βAPP immunoreactivity in blood is found only in platelets of both healthy and Alzheimer's patients. To further show that platelets were a circulating source of PN-2/βAPP, monoclonal antibody mAbP2-1 was used to effectively immunopurify PN-2/βAPP from platelet lysates to apparent homogeneity using a method similar to that of Example 1. The following is an example of one such immunopurification procedure.

EXAMPLE 18

Immunopurification of PN-2/βAPP from Platelets

Approximately 10 units of cutdated platelets were extensively washed and pelleted by centrifugation. They were then resuspended in 200 ml of 20 mM potassium phosphate, 0.15 M NaCl, pH 7.4 containing 1% Triton X-100, 5 mM EDTA, 500 µM phenylmethane sulfonylfluoride, 10 µM chymostatin and 10 µM tosyl phenylchloromethyl ketone and solubilized with a Polytron. The homogenate was centrifuged at 10,000 x g for 30 minutes at 4. C; the resulting supernatant was subjected to 40-80% ammonium sulfate precipitation. The 80% pellet was resuspended in 50 ml of 20mM potassium phosphate, 0.2 M NaCl, pH7.4, dialyzed against the same buffer and chromatographed over a 10 ml DEAE-Sepharose column. The adsorbed protein was eluted with 20 mM potassium phosphate, 0.2 M NaCl pH 7.4. The eluate was directly applied to a 3 ml immunoaffinity column of mAbP2-1-Sepharose, washed and eluted with 0.2 M glycine-HCl, 0.15 M NaCl, pH 2.7 followed by immediate neutralization with 2 M Tris-HCl, pH 8.0. Five µg of the immunopurified PN-2/βAPP from platelets were subjected to 10% nonreducing SDS-PAGE followed by staining with Coomassie Brilliant Blue. This gel is shown in FIG. 7, Panel C. It can be seen that the purified PN-2/βAPP co-migrates with the PN-2/βAPP immunoreactive species from Examples 15 and 16, Panels A and B respectively.

EXAMPLE 19

Western Blot of Purified PN-2/βAPP

Two µg of purified PN-2/βAPP from Example 18 was subjected to Western Blot as in Example 16, except that rabbit polyclonal antiserum (1:200) was used as the primary antibody. Bound antibody was detected as in Example 17. Results are shown in FIG. 7, panel D. Lane 1 shows rabbit polyclonal antiserum to synthetic A4. Lane 2 was as in Lane 1, absorbed with synthetic A4.

It can be seen from FIG. 7, panel D that the immunopurified PN-2/βAPP from platelet lysates was recognized by rabbit polyclonal antiserum to synthetic A4, demonstrating that at least part of the A4 protein is present in the PN-2/βAPP of platelet lysates.

Mechanism of PN-2/βAPP Release by Platelets

In order to elucidate the mechanism by which platelets can make PN-2/βAPP available, freshly washed platelets were treated with collagen or thrombin, physiologic platelet agonists that trigger secretion of platelet granule constituents. We discovered that activation of platelets with either collagen or thrombin resulted in secretion of approximately one-half of total PN-2/βAPP present in the platelets. Similarly, low affinity platelet factor-4 ("LA-PF4"), an α-granule constituent, and adenine nucleotides which are dense granule constituents, were also secreted after treatment of platelets with either agonist. To determine the extent that the presence of PN-2/βAPP or the granule markers in the releasates was due to platelet lysis, we assayed for the cytosolic marker lactate dehydrogenase ("LDH") which would only be expected to be released upon lysis. No LDH was detected in the releasates, demonstrating that the release of PN-2/βAPP did not result from platelet lysis. Treatment of the platelets with metabolic inhibitors prior to activation by either agonist blocked the secretion of PN-2/βAPP and the granule markers, consistent with findings that platelet activation and granule secretion are active processes. The methods of the foregoing experiments are described in the following Example.

EXAMPLE 20

Secretion of PN-2/βAPP from platelets

Secretion of PN-2/βAPP from platelets after activation by the agonists collagen or thrombin was studied. Briefly, fresh platelets washed by albumin density gradient centrifugation and gel filtration were incubated for 30 minutes at 37° C. in the absence or presence of the combined metabolic inhibitors antimycin A (15 µg/ml), 2-deoxy-D-glucose (30 mM), and D-gluconic acid δ-lactone (10 mM). The platelets were then placed into a cuvette 37° C. water bath with stirring at 1,200 rpm, and collagen (20 µg/ml or α-thrombin (1 U/ml) was added. After 10 minutes, the samples were centrifuged at 12,000 x g for 4 minutes and supernatants were collected. Aliquots were removed and quantitated for PN-2/βAPP by incubation with $^{125}$I-EGF BP and analysis of complex formation by SDS-PAGE and autoradiography as in Example 15. Autoradiograms were aligned with dried gels; $^{125}$I-EGF BP:PN-2/βAPP complexes were located, excised and quantitated in a 7 counter. Aliquots were also quantitated for platelet markers as follows: total adenine nucleotide (ADP/ATP) secretion was measured by the method of Homsen et al., *Anal. Biochem.*, 46:489 (1972); low affinity platelet factor 4 (LA-PF4) secretion was quantitated by the method of Rucinski et al., *Blood*, 53:47 (1979); and cytosolic lactate dehydrogenase (LDH) loss was assessed by the procedure of Wroblewski and Ladue, *Proc. Soc. Exper. Biol.*

Med., 77:389 (1978), the disclosures of which are hereby incorporated by reference. Results are summarized in Table III. Values represent the percent secreted. Percent secreted was determined from the ratio of releasate in agonist treated sample to the total amount present in detergent lysate; nonstimulated platelet supernatants were subtracted from both. Values expressed are the mean ±SEM of three experiments, each consisting of combined platelets from two donors.

The results of Table III suggested that PN-2/$\beta$APP was most likely a platelet granule protein. Therefore, we conducted further studies to ascertain the specific subcellular localization of PN-2/$\beta$APP. One study we conducted was platelet subcellular fractionation in order to ascertain in which fraction PN-2/$\beta$APP was found. The following example shows one such study.

EXAMPLE 21

Platelet Subcellular Fractionation by Differential Ultracentrifugation

A platelet pellet was prepared from 450 ml of blood, resuspended in 25 ml 10 mM HEPES, 1 mM EDTA, and 0.25 M sucrose and homogenized twice in a French pressure cell. Differential centrifugation of the homogenate, as described in Schmaier, et al., *J. Clin. Invest.*, 75:242 (1985), the disclosure of which is hereby incorporated by reference, resulted in four fractions: $F_1$, a 1,000 x g pellet which contained whole platelets and large platelet fragments; $F_2$, a 12,000 x g pellet which contained mitochondria and granules; $F_3$, a 100,000 x g pellet containing membranes, and $F_4$, a 100,000 x g supernatant containing cytosolic material. Aliquots of each fraction were quantitated for PN-2/$\beta$APP as described in Example 20; fibrinogen was quantitated by the method of Laurell, *Anal. Biochem.*, 15:45 (1966), the disclosure of which is hereby incorporated by reference; and LA-PF4 by the procedure of Rucinski et al., supra. Only preparations that had a recovery of at least 60% for total protein and each constituent were used in the analysis. The relative specific amounts of each marker in the preparation were calculated from the ratio of the specific amount of marker in the fraction (amount of antigen or activity per mg total protein) to the specific amount of the marker in the total platelet lysate according to the convention of de Duve et al, *Biochem J.*, 60:604 (1955), the disclosure of which is hereby incorporated by reference. The product of the relative specific amount of marker and percent total protein indicates the percent marker found within the fraction. FIG. 8A represents a bar graph of the percent of each marker SEM found within each fraction of the differential centrifugation.

FIG. 8A shows that approximately 53% of the total PN-2/$\beta$APP was recovered in the granule fraction $F_2$. Similar results were obtained for platelet fibrinogen and low affinity platelet factor-4, known $\alpha$-granule proteins. Thus, this granule preparation was further fractionated by sucrose density ultracentrifugation, as shown in the following example.

EXAMPLE 22

Platelet Subcellular Fractionation by Sucrose Density Ultracentrifugation

The granule fraction, F2, from Example 21, was further fractionated on a sucrose step gradient that increased from 0.8 to 2.0 M in 0.2 M increments. Centrifugation resulted in four major fractions: A, material which did not enter the gradient; B, lysosomal granule constituents; C, $\alpha$-granule constituents; and D, a pellet which consists of dense granules. PN-2/$\beta$APP and fibrinogen were quantitated as in Example 20. Serotonin was assayed by the procedure of Weissbach et al., *J. Biol. Chem.*, 230:865 (1955), the disclosure of which is hereby incorporated by reference. The data were calculated as in Example 21 and the results, shown in FIG. 8B, were plotted as in Example 21. Each bar graph, except for the serotonin, is the mean ±SEM of three experiments. The serotonin experiments are the mean of two identical experiments.

FIG. 8B shows that approximately 80% of the PN-2/$\beta$APP activity in the granule fraction $F_2$ was recovered in fraction C which is enriched for platelet $\alpha$-granules. Similar results were obtained for fibrinogen and low affinity platelet factor-4. In contrast, serotonin, a known dense granule constituent, was recovered almost exclusively in fraction D, a pellet of the sucrose gradient.

Thus, as the foregoing examples show, we have discovered that PN-2/$\beta$APP does not circulate freely in plasma, but is contained in the $\alpha$-granules of platelets. Moreover, the foregoing examples also show that we have further discovered that upon platelet activation, PN-2/$\beta$APP is secreted along with other platelet $\alpha$-granule constituents.

Diagnosis of Alzheimer's

The results of the foregoing studies on the circulating source of PN-2/$\beta$APP indicate a pathophysiologic mechanism for the deposition of cerebrovascular and peripheral perivascular PN-2/$\beta$APP and A4. In these situations, subtle changes in the vessel walls of the vasculature, as may occur in certain malformations, may expose sites that could activate platelets and cause them to secrete their granule contents, including PN-2/$\beta$APP and derived fragments, such as A4.

Platelets from individuals with Alzheimer's disease have alterations in their plasma membranes. We believe that this may contribute to increased platelet adherence to the vasculature and/or increased secretion of PN-2/$\beta$APP or related fragments. Therefore, we believe that platelets of Alzheimer's patients have altered levels of PN-2/$\beta$APP and related fragments. Due to the long lag time during which neuritic plaques are forming without causing symptoms, we believe that these altered levels of PN-2/$\beta$APP may be detectable years before clinical symptoms appear.

PN-2 $\alpha\nu\delta$ $\beta APP_{695sec}$ are believed to contain at least a portion of A4. It is believed that proteolytic cleavage of A4 occurs during normal processing of $\beta$APP. Thus, fragments of $\beta$APP slightly smaller than native PN-2 and $\beta APP_{695sec}$ may be present in pentelets. It is possible that there is an increase in this proteolytic cleavage in Alzheimer's disease. Thus, increased amounts of this smaller fragment may be present in Alzheimer's disease patients.

As stated above, one theory is that PN-2/$\beta$APP from Alzheimer's patients contains all of A4 while PN-2/$\beta$APP from normal subjects lacks at least a portion of A4. Thus, if this theory is correct, the detection of fragments of PN-2/$\beta$APP slightly larger than native PN-2 and/or $\beta APP_{695sec}$ by mAbP2-1 in Western assays would be indicative of Alzheimer's disease.

Accordingly, we have discovered methods for diagnosing Alzheimer's disease, which are effective not only prior to autopsy, but which are advantageously effective even prior to any clinical manifestations of the disease. One such method comprises obtaining platelets from a subject and determining the level of PN-2/βAPP or any fragment thereof in those platelets. An Alzheimer's patient will have significantly altered levels of PN-2/βAPP or a fragment thereof than normal subjects, even if the test is performed long before clinical manifestations appear.

Examples 23-27 are intended to illustrate typical methods of practicing this aspect of the present invention.

EXAMPLE 23

Determination of Normal Levels of PN-2/βAPP in Platelets

Ten healthy 20 year old female patients are tested for platelet levels of PN-2/βAPP by drawing 25 cc of blood from each. Platelets are isolated and lysed, and the level of PN-2/βAPP determined by the method of Example 10. The levels of PN-2 and $βAPP_{695sec}$ collectively are found to be in the range of 150 ng/$10^8$ platelets to 2 μg/$10^8$ platelets, with an average of μg/$10^8$ platelets. A much lower amount of a smaller fragment lacking all of the A4 region is detected.

EXAMPLE 24

Detection of Alzheimer's Disease through Platelet Levels of PN-2/βAPP

A 60 year old female patient with no clinical symptoms of Alzheimer's disease is tested for Alzheimer's by drawing 25 cc of blood. Platelets are isolated and lysed, and the level of PN-2 and $βAPP_{695sec}$ determined by the method of Example 10. The level of PN and $βAPP_{695sec}$ collectively is found to be lower than the normal levels of determined in Example 23. The patient shows a higher level of the smaller fragment of PN-2/βAPP lacking the A4 region. The patient shows detectable levels of the larger fragment of PN-2/βAPP having all of the A4 region. Thus, it is concluded that the patient has a high potential for developing Alzheimer's symptoms within the next few years. Appropriate treatment may then be provided.

Thus, the foregoing examples show quantitative and qualitative methods of the present invention in which platelet levels of the various fragments of PN-2/βAPP are indicative of Alzheimer's disease. These examples show that quantitative changes in the levels of PN-2 and $βAPP_{695sec}$ may be used to diagnose Alzheimer's disease. Additionally, the qualitative findings of either the larger fragment of PN-2/βAPP containing most or all of the A4 region or the smaller fragment lacking the A4 region may also be indicative of Alzheimer's disease.

An additional method of the present invention is to detect Alzheimer's disease by altered levels of PN-2/βAPP in the CSF. An example of this method is shown in Example 25.

EXAMPLE 25

Determination of Normal Levels of PN-2/βAPP in CSF

Four healthy patients were tested for levels of PN-2/βAPP by drawing 3 cc of CSF from each. The level of PN-2/βAPP in each sample was determined by the method of Example 10 and by the method of Example 20. The levels of PN-2/βAPP were found to be in the range of 5 to 10 μg/ml, with an average of 7.5 μg/ml.

EXAMPLE 26

Detection of Alzheimer's Disease through CSF Levels of PN-2/βAPP

Four patients with varying clinical symptoms of Alzheimer's disease were tested for Alzheimer's by drawing 3 cc of CSF. The level of PN-2/βAPP in the CSF was determined by the method of Example 10. The level of PN-2/βAPP was found to be at least 50% lower than the normal levels determined in Example 25. Thus, the decreases in PN-2/βAPP in CSF correlated with neurodegeneration.

Thus, Example 26 shows a method of the present invention in which CSF levels of PN-2/βAPP are indicative of Alzheimer's disease. We also believe that the increased secretion of PN-2/βAPP in Alzheimer's patients results in PN-2/βAPP being detectable in a wide variety of tissues in these patients. Thus, additional methods of the present invention may detect Alzheimer's disease by detecting altered levels of PN-2/βAPP in the any of a wide variety of tissues. Some particular tissues are believed to have normal levels of PN-2/βAPP that are substantially undetectable by the methods of the present invention in healthy patients, yet have elevated levels in Alzheimer's. Thus, for these tissues, the detection of any PN-2/βAPP is indicative of a disease state. These tissues include skin, subcutaneous tissue and intestine. It has been found that these tissues have normal levels of PN-2/βAPP in the range of 1 pg/mg tissue to 5 pg/mg tissue. The following example illustrates a method embodying this aspect of the present invention.

EXAMPLE 27

Detection of Alzheimer's Disease through the Presence of PN-2/βAPP

A 62 year old male patient with no clinical symptoms of Alzheimer's disease is tested for Alzheimer's by first obtaining a small sample of skin from the top of the hand. The skin is homogenized and the level of PN-2/βAPP in the homogenate is determined by the method of Example 10. The level of PN-2/βAPP is found to be 0.5 pg/mg tissue. Thus, it is concluded that the patient has a high potential for developing Alzheimer's symptoms within the next few years. Appropriate treatment may then be provided.

Thus, Examples 23 through 27 demonstrate that detecting altered levels of PN-2/βAPP in various body fluids and tissues may be used to diagnose AD.

In order to more definitively diagnose AD, we have discovered a highly specific and sensitive assay for PN-2/βAPP in the CSF. The assay involves an immunoassay for PN-2/βAPP using a monoclonal antibody raised against purified native PN-2/βAPP, e.g. monoclonal antibody mAbP2-1, described above.

We have discovered that very small quantities, i.e. 100 μl or less, of CSF contain significant immunoreactivity towards monoclonal antibody raised against purified native PN-2/βAPP. Thus, use of monoclonal antibodies raised against purified native PN-2/βAPP in an immunoassay for PN-2/βAPP, advantageously, allows the use of small quantities of unconcentrated CSF. This is in contrast to previously known assays for PN-2/βAPP which required concentration of relatively large volumes of CSF. Significantly, the use of small volumes of unconcentrated CSF prevents excessive amounts of protein from competing for binding to the solid phase support used in ELISA and other immunoassay techniques. Additionally, the use of concentrated and/or dialyzed samples as in previous assays can contribute to PN-2/βAPP proteolysis. Thus, the sensitivity of assays for PN-2/βAPP using monoclonal antibodies raised against purified native PN-2/βAPP is increased further through use of the appropriate microliter quantities of CSF. Preferably, assays are performed using CSF samples in the range 0.5 μl to 100 μl, more preferably 2 μl to 20 μl, and still more preferably in the range 2 μl to 10 μl.

Preferably, when an assay for CSF levels of PN-2/βAPP is used to aid in the diagnosis of AD, the samples are collected by lumbar puncture. We have observed significant variability with cerebrospinal fluid samples collected from the brain ventricles at autopsy.

An important advantage of the sensitivity obtained through use of monoclonal antibodies raised against native purified PN-2/βAPP in immunoassays for PN-2/βAPP is the reliability of the data obtained therefrom. Thus, the detection of lowered levels of PN-2/βAPP in a particular sample of CSF from a patient, is highly indicative of the presence of AD in that patient when such assays are used with an appropriate volume of CSF. This is in contrast to previously known assays, in which altered levels of PN-2/βAPP could be detected in populations of AD patients compared to control populations, but not between individuals. Another important advantage of the assay resulting from its reliability is that it can assist in distinguishing between AD and dementia of other causes, such as vascular dementia; only the AD patients would be expected to have reduced levels of PN-2/βAPP. Examples of assays providing reliable data as described above are shown in Examples 28 and 29.

EXAMPLE 28

PN-2/βAPP Enzyme-Linked Immunosorbent Assay

A. Selection of Subjects

Fifteen probable Alzheimer's disease patients, 18 demented (non-Alzheimer type) controls, and 16 normal healthy individuals underwent lumbar puncture to obtain CSF samples. The probable Alzheimer's disease group consisted of 8 men and 7 women, 50 to 78 years of age (mean, 65). The diagnosis of probable Alzheimer's disease conformed to the National Institute for Neurological and Communicative Disorders plus Stroke (NINCDS)/Alzheimer's Disease and Related Disorders Association (ADRDA) criteria. The battery included the full Consortium to Establish a Registry for Alzheimer's Disease (CERAD) evaluation with additional tests for a more comprehensive neuropsychological examination. Each patient's medical history was obtained and reviewed, a complete physical and neurological examination was performed and approximately thirty psychometrics assessing global cognitive function, intelligence, language, memory, visual-spatial skills, and frontal lobe skills were administered. In addition, biochemical analyses on blood and urine, a chest roentgenogram, and electrocardiogram were performed. These tests allowed the diagnosis of organic versus non-organic causes of dementia. Each patient had a series of magnetic resonance imaging scans consisting of $T_1$-weighted sagittal, $T_2$-weighted axial, and inversion recovery coronal planes of section. The coronal images through the temporal lobe were used to visualize the hippocampus, a structure particularly vulnerable to Alzheimer's disease. Finally, single photon emission computerized tomography was employed using the HMPAO +/− Xenon methods to examine blood flow and cerebral metabolism as a further method to differentiate between vascular and degenerative dementia.

Based on the foregoing criteria, probable AD patients were selected who exhibited strong indications for typical AD and did not present evidence for another basis for their dementia. Those patients that had a clear history of risk factors, a neuropsychometric profile inconsistent with AD, and evidence of vascular and/or other involvement based on imaging and scanning analyses were labeled as probable non-Alzheimer's dementia. However, it should be emphasized that some of these patients should still be designated as possible AD, and a subset of this group is most likely afflicted with both forms of dementia.

The demented (non-Alzheimer type) group consisted of 12 men and 6 Women, 59 to 78 years of age (mean, 71). This group consisted of 14 diagnosed probable vascular dementia patients, patient with a combination of vascular dementia, a history of alcohol abuse and probable Wernicke-Korsakoff's syndrome, 2 patients diagnosed with fronto-temporal lobe dementia and 1 patient diagnosed with transient global amnesia. The non-demented controls consisted of 5 men and 11 women, 29 to 82 years of age, (mean 62); none had any acute or chronic illness or reported any symptoms related to Alzheimer's or vascular disease.

B. Cerebrospinal Fluid Collection

Without knowledge of the specific dementia, a neurologist collected cerebrospinal fluid from each patient who did not appear too debilitated or fragile to safely undergo a lumbar puncture. Lumbar puncture was sterilely performed using a 20 gauge needle and 1.0% Xylocaine as a local anesthetic. Volumes of 3 to 5 μl were collected; cell counts and assays for glucose, protein and IgG levels were done to exclude any routine cerebrospinal fluid abnormalities. The protein concentrations in each sample were determined using an automated ACA analyzer (DuPont). Samples were aliquoted and stored at −70° C. until assayed.

C. Assay for PN-2/βAPP

Triplicate samples containing 5 to 10 μl of CSF or known quantities of purified PN-2/βAPP were coated on 96-well microtiter plates overnight at 4° C. The CSF was removed by aspiration and the remaining unoccupied sites in the wells were blocked with a solution of phosphate-buffered saline containing 1.0% ovalbumin for 30 minutes at room temperature. This blocking solution was removed and the wells were washed three times with phosphate-buffered saline containing 0.05% Tween-20. After washing, 100 μl of mouse monoclonal mAbP2-1 (10 μg/ml) was added to each well and incubated at 37° C. for 1 hour with shaking. The hybridoma culture medium was removed and the wells were washed three times with phosphate-buffered saline containing 0.05% Tween-20. After washing, bound mouse monoclonal antibody was detected with a solution (1:400) of biotinylated-goat anti-mouse IgG that was adsorbed with human serum (Sigma, St. Louis, MO) and a solution (1:800) of streptavidin-horseradish peroxidase conjugate (Amersham, Arlington Heights, Ill.) in phosphate-buffered saline containing 1.0% ovalbumin with the above washing protocol performed after each step. The assay was developed by the addition of 100 µl/well of a solution of 10mM o-phenylenediamine, 0.1M sodium citrate, pH 4.5, containing 0.012% $H_2O_2$. The reactions were quenched with 50 µl/well of 4N $H_2SO_4$ and the absorbance at 492 nm was recorded with a Titertek Multiskan (Flow Laboratories, McLean Va.). Values obtained from the CSF samples were compared to standard curves generated from known quantities of purified PN-2/βAPP.

D. Results

Results are shown quantitatively in Table IV with, individual data points shown graphically in FIG. 9. The enzyme-linked immunosorbent assays with monoclonal antibody mAbP2-1 showed that the probable Alzheimer's patients as a group had lower average cerebrospinal fluid levels of PN-2/βAPP (0.8±0.4 µg/ml) than did the demented (non-Alzheimer type) controls (2.9±1.0 µg/ml) and the normal healthy individuals (2.7±0.7 µg/ml). The demented (non-Alzheimer type) group had PN-2/βAPP levels slightly higher than those observed in the non-demented control group, with the levels in the demented (non-Alzheimer type) group being at approximately 111% of the levels observed for the non-demented control group. In contrast, the cerebrospinal fluid levels of PN-2/βAPP in the probable Alzheimer's patients were at levels approximately 28% and 29%, respectively, of the levels in the demented (non-Alzheimer type) group and the non-demented control group.

We did not observe a general decrease in the cerebrospinal fluid levels of PN-2/βAPP with respect to age in the control populations. In fact, some of the older individuals had the highest cerebrospinal fluid levels. The cerebrospinal fluid total protein concentrations were similar in all three populations demonstrating that the decreased PN-2/βAPP levels in the probable Alzheimer's patients were not due to a decrease in total protein content. As seen in the right-hand column of Table IV, when the levels of PN-2/βAPP were standardized to total cerebrospinal fluid protein, the decrease in PN-2/βAPP in the Alzheimer's patients was even greater.

One particular seventy-five year old patient, diagnosed with probable Alzheimer's disease, had a cerebrospinal fluid PN-2/βAPP concentration of 1.1 µg/ml. Two months after the cerebrospinal fluid was collected, this patient died and another sample was collected at autopsy by lumbar puncture. Enzyme-linked immunosorbent analysis of this post mortem sample revealed a concentration of 1.0 µg/ml. Post-mortem neuropathological examination of the brain confirmed that this individual had Alzheimer's disease.

Advantageously, as best seen in FIG. 9, every individual AD patient had a level of PN-2/βAPP significantly lower than the lowest level of PN-2/βAPP seen in the non-demented control group. Thus, it can be seen that the assay of this Example reliably distinguishes between the non-demented controls and AD. In addition, every individual AD patient tested also had a lower level of PN-2/βAPP than the demented (non-Alzheimer type) group. Thus, the assay also appears to reliably distinguish between Alzheimer's type dementia and other forms of dementia. Together, these findings indicate that determining the cerebrospinal fluid levels of PN-2/βAPP can distinguish between probable Alzheimer's patients and demented (non-Alzheimer type) controls and nondemented controls.

In order to confirm the results obtained in the ELISA assay of Example 28, we performed an immunoblot analysis using the same monoclonal antibody. These assays are described in Example 29.

EXAMPLE 29

PN-2/βAPP Immunoblot Analysis 2.5 µl aliquots of CSF were diluted to 25 µl in PBS and 25 µl of 2× sample buffer was added. The samples were subjected to nonreducing SDS-PAGE. The completed gels were electroblotted onto polyvinylidene difluoride membranes (millipore) for 1.5 hours at 400 milliamps in a Transblot unit (BioRad Laboratories). The membranes were gently agitated overnight at room temperature in a solution of PBS containing 0.25% gelatin to block unoccupied sites, and then incubated with a solution of mAbP2-1 (10 µg/ml) for 1 hour at 37° C. with gentle agitation. After several washes with PBS containing 0.05% Tween-20, bound mouse mAb was detected with a solution of $^{125}$I-labeled affinity purified goat anti-mouse $IgG_1$ (100 ng/ml); $1.5 \times 10^5$ cpm/pMole) in PBS containing 0.25% gelatin. After several washes with PBS containing 0.05% Tween-20, the membranes were dried and exposed to X-ray film at −70° C. for 1-2 hours. Autoradiograms were quantitated by an LKB scanning laser densitometer.

The immunoblot resulting from the procedure of Example 29 is shown in FIG. 10A. The relative amount of immunoreactivity in each of the lanes of FIG. 10A, as measured by optical density scanning, is shown in FIG. 10B. This immunoblot identifies the prominent PN-2/βAPP species at 116 kD that is detected in cerebrospinal fluid. It is noteworthy that monoclonal antibody mAbP2-1 recognizes forms of the amyloid β-protein precursor that contain or lack the Kunitz protease inhibitor domain. Importantly, FIG. 10A also demonstrates that our monoclonal antibody mAbP2-1 does not cross-react with any other proteins in the cerebrospinal fluid samples, thus validating the results obtained in our enzyme-linked immunosorbent assay. The nondemented control group (lanes 1-3) and the demented (non-Alzheimer type) group (lanes 4-6) exhibited similar immunoreactivity on the immunoblot. In contrast, the probable Alzheimer's group (lanes 7-9) showed significantly lower immunoreactivity on the immunoblot (approximately 3.5-fold lower), consistent with the findings of the enzyme-linked immunosorbent assay. Thus, this immunoblot analysis supports the results provided by the ELISA of Example 28 that use of monoclonal antibody raised against purified native PN-2/βAPP can provide a reliable assay to aid in the diagnosis of AD.

In order to verify that the ELISA results were reflective of relative PN-2/βAPP levels, we tested the ELISA using known quantities of purified PN-2/βAPP. FIG. 11A shows that the ELISAs using mAbP2-1 and purified PN-2/βAPP coated on tissue culture-treated 96-well microtiter plates showed a strong linear correlation between reaction absorbance at 492 nm and quantity of antigen. Cationically charged tissue culture-treated microtiter plates were used because of their selective binding of PN-2/βAPP which contains a highly anionic domain. FIG. 11A also shows that added exogenous PN-2/βAPP to control or AD CSF is completely recovered in the ELISA, further demonstrating the selective binding of PN-2/βAPP to the tissue culture-treated plates.

In order to determine if other negatively charged CSF proteins would interfere in our ability to measure PN-2/βAPP we conducted ELISAs with known quantities of PN-2/βAPP in the presence and absence of control and AD CSF. The results of these analyses are shown in FIG. 11B, which shows that even in the presence of control and AD CSF, we recovered total amounts of exogenously added PN-2/βAPP. Thus, even under these conditions, total CSF PN-2/βAPP is adsorbed to the microtiter plates.

The results obtained in our studies show a more dramatically pronounced decrease in CSF PN-2/βAPP levels in AD patients than have other recent studies, such as Prior, R. et al., Neurosci. Lett. 124:69–73 (1991) and Henriksson, T. et al., J. Neurochem. 56:1037–1042 (1991). In order to understand the basis for these differences we conducted parallel ELISA studies on purified PN-2/βAPP and representative CSF samples using our mAbP2-1 and mAb22C11, which was used in the study by Prior, R. et al. FIG. 12A shows the dose-dependent recognition of PN-2/βAPP by each of these antibodies in these ELISA studies, with mAb22C11 shown with open circles and mAbP2-1 shown in darkened circles. It can be seen that mAb22C11 recognized PN-2/βAPP in linear dose-dependent fashion, but with a three-fold less intensity than mAbP2-1. It is noteworthy that similar results were obtained in ELISAs with PN-2/βAPP proteins purified from control and AD CSF (data not shown). However, we also conducted ELISAs using both mAb22C11 and mAbP2-1 on CSF samples as described in Example 28C. The results of these studies are shown in FIG. 12B, with results using mAb22C11 shown in solid bars and results using mAbP2-1 shown in striped bars. It can be seen that in these ELISAs, mAb22C11 yielded even lower signals when compared to parallel ELISAs with mAbP2-1.

Furthermore, the differences in CSF PN-2/βAPP levels observed between AD patients and the demented (non-Alzheimer type) patients and non-demented controls were much less apparent in the ELISAs with mAb22C11. These findings, together with our findings that mAbP2-1 is highly specific for PN-2/βAPP, suggest that the previously reported smaller differences in CSF PN-2/βAPP levels in AD patients compared to non-demented controls and demented (non-Alzheimer type) patients is likely to be the result of the sensitivity and specificity of the antibodies employed in the present invention.

While not wishing to be bound by any particular mode of action, our finding that lowered levels of PN-2/βAPP are reliably found in the CSF of AD patients suggests that altered proteolytic mechanisms occur in AD such that the integrity of the portion of PN-2/βAPP binding to mAbP2-1 is maintained. It should be noted that our monoclonal antibody recognizes an amino terminal epitope on PN-2/βAPP and will recognize forms of the protein with or without the Kunitz inhibitory domain. In addition, mAbP2-1 recognizes a previously described 25 kD amino terminal PN-2/βAPP fragment that is present in brain and CSF. Since the putative proteolytic events discussed herein are believed to occur in brain, it is believed that they result in altered levels of the PN-2/βAPP in the CSF which bathes the brain.

It should be noted that the forms of PN-2/βAPP measured in CSF are the secreted, processed forms, principally PN-2 and $APP_{695sec}$ (as these terms are defined in the paragraph following Example 5). It is further noteworthy, from our findings reported hereinbelow at Example 33, that it is the $APP_{695sec}$ form of PN-2/βAPP which is significantly reduced in the CSF of AD patients relative to normals. On the other hand, PN-2, the processed, secreted form of PN-2/βAPP containing the Kunitz protease inhibitory domain, remains relatively stable in both AD patients and patients with another amyloidosis.

Diagnosis of other Amyloidoses

Normal constitutive processing of PN-2/βAPP involved with release of its large extracellular domain has been shown by others to be the result of cleavage through the A4 domain. We believe that this finding indicates that abnormal proteolytic events occur in diseases that involve cerebrovascular deposition of amyloid which result in the integrity of the A4 domain being maintained. We believe that this is a feature common to diseases associated with cerebrovascular deposition of amyloid. (These disease are referred to herein plurally as "amyloidoses" and singularly as "amyloidosis".) Accordingly, we have discovered that the methods described herein in connection with the diagnosis of AD can be applied in the diagnosis of other amyloidoses.

Hereditary cerebral hemorrhage with amyloidosis-Dutch type ("HCHWA-D") is one such other amyloidosis. This disease is a rare form of cerebral amyloid angiopathy described in four families in the Netherlands. Patients with this disease usually develop recurrent and often fatal intracerebral hemorrhages by the fifth or sixth decade of life. HCHWA-D is characterized by extensive deposition of the amyloid in the vessel walls of the meningeal and cortical arterioles. Amyloid deposits that resemble early senile plaques of AD have also been observed in the parenchyma of some patients. Individuals with HCHWA-D have previously been shown to have a point mutations in their gene coding for PN-2/βAPP which results in a glutamine for glutamic acid substitution in the A4 domain. This mutation is postulated to play a role in the abnormal proteolysis of PN-2/βAPP, leading to the formation and deposition of A4.

We studied the ability of the methods of the present invention to detect other amyloidoses by applying the methods to HCHWA-D patients. These studies are shown below in the following examples.

EXAMPLE 30

Initial Diagnosis of HCHWA-D

Initial diagnosis of HCHWA-D was based on an extensive family history of the disease supported by clinical and pathological findings that included evidence for one or more cerebral hemorrhages confirmed by computerized tomography and nuclear magnetic resonance imaging. In addition, each HCHWA-D patient in this example exhibited the point mutation in their PN-2/βAPP gene, as demonstrated by single stranded conformation polymorphism in connection with polymerase chain reaction (PCR). Single stranded conformation polymorphism detection is described by Orita et al., Proc. Natl. Acad. Sci. U.S.A., 84:2766–2779 (1988). This is a rapid and sensitive technique for visualizing point mutations in genomic DNA. PCR was performed for 26 cycles using the primer pairs 5'-TCAG-TATATTCTCTGCCAAC-3' and 5'-AGACTAT-GAGACAATTAGGC-3' using a small amount of $^{32}$P- dCTP in addition to each non-labelled nucleotide triphosphate. The PCR products were then diluted 100-fold and subjected to SDS-PAGE. The resulting gel was transferred to Whatman 3M paper, dried, and exposed to X-ray film with an intensifying screen overnight at −70° C. to visualize the conformation of the single stranded 355 base pair PCR products. The resulting autoradiogram is shown in FIG. 13. FIG. 13 shows that all three HCHWA-D patients (lanes 1–3) showed the same single stranded conformation polymorphism variation, as indicated by arrow, which was not present in 50 normal individuals. A single normal individual is shown in lane 4.

Thus, the results of Example 30 confirm that these three live patients carried the HCHWA-D mutation and were clinically manifesting the disease. We conducted immunoblotting studies to quantitatively analyze the CSF PN-2/βAPP levels in these patients. These studies are shown in Example 31.

EXAMPLE 31

Immunoblot Quantitation of PN-2/βAPP in CSF

20 μl aliquots of CSF from each patient were subjected to immunoblotting with mAbP2-1 as described in Example 29. Molecular weights were determined with low range prestained standards available from BioRad Laboratories. The resulting immunoblot is shown in FIG. 14A. Lanes 1–3 contained samples from age-matched normals, lanes 4–6 contained samples from the three HCHWA-D patients identified in Example 30, and lanes 7–9 contained samples from probable AD patients diagnosed as described above in Example 28. The normals and probable AD patients were age-matched with the HCHWA-D group.

The resulting immunoblot demonstrates that mAbP2-1 recognized only a single band in the CSF having an apparent mobility the same as PN-2/βAPP. This result supports the use of this antibody in the ELISA assays for PN-2/βAPP described herein. A similar gel was run using 2.5 μl aliquots of CSF and PN-2/βAPP proteins were quantified using an LKB scanning laser densitometer. The results of this quantitation are shown in the bar graph of FIG. 14B.

It can be seen qualitatively in the immunoblot of FIG. 14A, and quantitatively in the bar graphs of FIGS. 14B, that CSF from both HCHWA-D and AD patients contained significantly less PN-2/βAPP than the age-matched controls. To confirm these results, we performed ELISA experiments using the same antibody. These ELISA experiments are shown in the following example.

EXAMPLE 32

ELISA Quantitation of PN-2/βAPP in CSF

Triplicate samples containing 5 μl of CSF or known quantities of PN-2/βAPP were diluted to a final volume of 100 μl in PBS and coated on Corning tissue culture-treated 96-well microtiter plates overnight at 4° C. ELISA was conducted with mAbP2-1 as described in Example 28. To determine APP concentrations, values obtained from the CSF samples were compared to standard curves generated from the samples containing known quantities of purified PN-2/βAPP. The results are shown in FIG. 14C, where the various lanes have the same designations as in FIGS. 14A and 14B, described in connection with Example 31. The values shown for each patient represent the mean ±SEM of the three separate ELISA experiments. It can be seen from the results in FIG. 14C that the ELISA confirms the results of the immunoblots that PN-2/βAPP levels in CSF are significantly reduced in both HCHWA-D and AD patients.

The data from the ELISA experiments of Example 32 is summarized in Table V. These data show that the normals had CSF PN-2/βAPP levels approximately 4-fold and 3-fold higher than the HCHWA-D patients and the probable AD patients, respectively. The CSF total protein content was similar in all three groups, demonstrating that the decreases in PN-2/βAPP levels in the HCHWA-D and probable AD patients were not due to a decrease in total CSF protein.

Prior et al. (supra) and Henriksson et al. (supra) have reported that the form of PN-2/βAPP which lacks the Kunitz Protease Inhibitor (KPI) domain (mostly $APP_{695sec}$) accounts for over 90% of the total PN-2/βAPP in the CSF. We performed quantitative protease complex formation assays that are specific for KPI-containing forms of PN-2/βAPP, which consist mostly of PN-2.

EXAMPLE 33

Quantitation of KPI-Containing PN-2/βAPP (PN-2)

25 μl aliquots of CSF samples or 3 ng purified PN-2/βAPP were incubated with 20 ng of $^{125}$I-labeled epidermal growth factor binding protein ($8.5 \times 10^5$ cpm/pmole) for 15 minutes at 22° C. The reactions were terminated by the addition of 2× nonreducing Laemmli sample buffer and the entire samples were electrophoresed on 7.5% acrylamide gels under nonreducing conditions without prior boiling of the samples. Completed gels were stained, dried and exposed to X-ray film with an intensifying screen for 4 hours at −70° C. to visualize the radiolabeled protease:PN-2/βAPP complexes.

The resulting autoradiogram is shown in FIG. 15. Lanes 1–3 contained samples from age-matched normals, lanes 4–6 contained samples from HCHWA-D patients, lanes 7–9 contained samples from probable AD patients and lane 10 contained purified PN-2/βAPP. High molecular weight radiolabeled protease:PN-2/βAPP complexes are indicated by the arrows.

Radiolabeled protease:PN-2/βAPP complexes were quantitated from autoradiograms using an LKB scanning densitometer. Values for protease:PN-2/βAPP complexes obtained from the CSF samples were compared to standard curves of radiolabeled complexes obtained using the known quantities of purified PN-2/βAPP. These values are reported in Table V under "KPI-containing APP". In addition to the data reported in Table V, we conducted additional measurements with CSF samples from 7 normals and 8 probable AD patients. These additional studies yielded similar results ($0.085 \pm 0.038$ μg/ml for the normals and $0.081 \pm 0.041$ μg/ml for the probable AD patients). The amounts of PN-2/βAPP lacking the KPI domain can be determined by subtracting these values from the total amounts of PN-2/βAPP in the CSF.

Thus, Example 33 reveals that the levels of these minor CSF PN-2/βAPPs, which consist mostly of PN-2, were similar in normals, HCHWA-D and probable AD patients. Together with the findings of Example 32, we have shown that we can identify CSF PN-2/βAPP levels at significantly decreased levels in live patients with HCHWA-D disease and probable AD compared to age-matched normals and that these decreased levels are selective for the form of PN-2/βAPP that lacks the KPI domain.

Thus, it appears from the data of Example 33, that the CSF of non-amyloidogenic patients contains relatively high levels of $APP_{695sec}$, the "correctly" processed form of the major PN-2/βAPP lacking the KPI domain, compared to AD or HCHWA-D patients. At the same time, it appears that levels of PN-2, the "correctly" processed form of the major PN-2/βAPP containing the KPI domain, are unchanged in patients with these amyloidogenic diseases relative to normals.

In view of the findings of Example 33, we believe that the amounts of PN-2/βAPP lacking the KPI domain in CSF are still more precise at indicating the presence of an amyloidogenic disease state than the total PN-2/βAPP levels due to the elimination of the background level of KPI containing forms. Accordingly, in one aspect of the present invention, levels of the non-KPI-containing form of PN-2/βAPP are measured in order to diagnose an amyloidosis associated with cerebrovascular deposition of PN-2/βAPP, such as AD. If the measured levels are lower than normal levels, then an amyloidosis is likely to be present. The level of non-KPI-containing form of PN-2/βAPP can be measured through a variety of methods. For example, the level of the KPI-containing form of PN-2/βAPP can be measured and subtracted from the total amount of PN-2/βAPP. This can be accomplished through an assay for protease:precursor protein complex formation, as in Example 32, or through an immunoassay using an antibody directed to an epitope unique to the KPI domain. Alternatively, the level of the KPI-containing form of PN-2/βAPP can be measured directly through any method known to those of skill in the art for measuring levels of a known protein.

Recent studies by us and others suggest that both HCHWA-D and AD involve abnormal proteolytic processing of PN-2/βAPP, leading to formation of the A4 protein and its deposition in the brain parenchyma and vessel walls of the cerebrovasculature. Although A4 is found in numerous neuritic plaques within certain regions of AD brain, only a few "diffuse" plaques have been demonstrated in brain from HCHWA-D patients. The reported absence of neurofibrillary tangles and neuritic plaques in HCHWA-D patients suggests that neuropathological differences exist between the two diseases. However, recent studies have demonstrated a greater abundance of "diffuse" plaques and some neuritic plaques in postmortem brain tissue from these patients. The parallel found here in lowered levels of PN-2/βAPP in the CSF of both HCHWA-D and AD patients establishes a pathogenic link between the two diseases and emphasizes the importance of HCHWA-D as a model to investigate certain aspects of AD.

Our findings that levels of "correctly" processed forms of PN-2/βAPP are reduced in amyloidogenic diseases are consistent with the numerous observations that suggest that AD and HCHWA-D patients have large amounts of the A4 protein in their neuronal parenchyma and cerebrovasculature. Our results support our conclusion that excess A4 results from "incorrect" processing of PN-2/βAPP. This is because in order for there to be large amounts of incorrectly processed forms of PN-2/βAPP, there should be relatively low amounts of the "correctly" processed forms of PN-2/βAPP, such as $APP_{695sec}$. Thus, it is likely that production of A4 results from improper processing of the 695 amino acid (non-KPI-containing) form of PN-2/βAPP.

Our results with AD and HCHWA-D patients show a striking parallel to individuals with hereditary cerebral hemorrhage with amyloidosis (Icelandic-type) ("HCHWA-I"), another disease where an amyloidogenic fragment is generated from a protease inhibitor precursor molecule. The amyloid formed in HCHWA-I is the result of proteolytic processing of a variant form of the cysteine protease inhibitor cystatin-C. Individuals with HCHWA-I have a point mutation in their cystatin C gene which leads to altered proteolysis of the protein and deposition of an amyloid fragment in the vessel walls of the cerebrovasculature. Grubb et al., N. Engl. J. Med., 311:1547–1549 (1984), have shown that levels of cystatin C three-fold lower than normal controls can be found in the CSF of individuals with HCHWA-I.

Thus, we believe that proteolysis of a variant or abnormally processed amyloid precursor proteins, such as PN-2/βAPP and cystatin-C, leads to the reduction in the cerebrospinal fluid levels of amyloid precursor protein in diseases characterized by cerebrovascular deposition of amyloid. While not wishing to be bound by any particular theory of mechanism of action, we believe that the decreased levels of amyloid precursor proteins in the CSF of individuals affected by diseases associated with cerebrovascular deposition of amyloid results from increased proteolysis of mutated and/or abnormally processed precursor proteins that occur in such diseases. Based on the findings presented herein, we believe that this mechanism represents a common feature in many or all such amyloidoses. Thus, we believe that many amyloidoses associated with altered processing of PN-2/βAPP can be detected by measuring CSF levels of this amyloid precursor protein in accordance with the methods described herein in connection with AD and HCHWA-D. In accordance with the findings discussed herein regarding lowered CSF levels of cystatin-C in HCHWA-I, we also believe that amyloidoses associated with amyloid precursor proteins other than PN-2/βAPP can be diagnosed by measuring lowered CSF levels of the corresponding amyloid precursor protein in affected individuals. Advantageously, the methods of the present invention can be used before clinical manifestations of the amyloidosis, such as plaque deposition and the resulting neurological dysfunction, appear.

The methods described herein can also be used to determine whether a known disease is associated with altered processing of amyloid precursor protein. Thus, CSF levels for a variety of amyloid precursor proteins can be measured in a number of individuals suffering from a disease suspected of being associated with cerebrovascular deposition of amyloid. These levels can be compared to normal levels of these proteins. If the disease is in fact associated with altered processing of amyloid precursor protein, lowered levels of a particular amyloid precursor protein will be identified.

An alternative method of identifying the amyloid precursor protein associated with a particular amyloidosis is to obtain a sample of cerebrovascular amyloid deposits from a patient suffering from the disease and identifying amyloid precursor proteins found therein. This can be accomplished by measuring immunoreactivity to a variety of antibodies raised against different amyloid precursor proteins. Significant levels of immunoreactivity will be found of the amyloid precursor protein present in the deposits.

No such antibodies are available for amyloid precursor proteins not previously identified as such. Thus, these novel amyloid precursor proteins can be identified by biochemical characterization of proteins found in the amyloid deposit, in accordance with methods known to those of ordinary skill in the art.

Once a particular amyloid precursor protein has been identified which is associated with a particular disease involving cerebrovascular deposition of amyloid, then the methods of the present invention can be used to identify other individuals suspected of being affected by the disease. To diagnose such individuals, CSF levels of the identified protein will be compared with normal controls, with lower levels of the identified protein being indicative of the presence of the disease. The determination of CSF levels of proteins other than PN-2/$\beta$APP can be made using immunoblot assays, ELISA assays or other immunological assays, such as those developed in accordance with the methods described herein in connection with PN-2/$\beta$APP.

Coagulation Inhibition

Our discoveries that PN-2/$\beta$APP is an $\alpha$-granule constituent of platelets and that it may be secreted upon platelet activation are particularly significant when combined with recent reports that PN-2/$\beta$APP possesses growth factor activity. It is known that platelets aggregate at wound sites and secrete the contents of their storage granules which include growth factors. Moreover, wound sites also contain elevated levels of proteases which: (a) mediate formation of the fibrin clot, (b) participate in tissue repair by stimulating cell division and cell migration, and (c) influence inflammatory response. Thus, we believe that PN-2/$\beta$APP, which has both protease inhibitory activity and growth factor activity is involved in the complex events that lead to tissue repair.

In particular, PN-2/$\beta$APP has Factor XIa inhibitory activity. The kinetic studies of Example 8, reported in Table II, show that PN-2/$\beta$APP is a potent inhibitor of coagulation factor XIa, suggesting that PN-2/$\beta$APP may be a modulator of the blood clotting cascade. Factor XIa is critical in the events leading to blood coagulation. The inhibition of Factor XIa blocks nearly the entire cascade. Thus, we have discovered that PN-2/$\beta$APP can be successfully used as an anti-coagulation agent in mammals. Anti-coagulation treatment is useful in treating a variety of diseases in which blood clots may cause severe disabilities, such as myocardial infarction, phlebitis, stroke and other diseases.

Accordingly, in certain preferred embodiments of the present invention, PN-2/$\beta$APP or an analog thereof is formulated into pharmaceutical preparations having anti-coagulation activity. These pharmaceutical preparations may further include other pharmaceutically active ingredients. In addition, any of the well-known pharmaceutically acceptable carriers or excipients may be combined with PN-2/$\beta$APP in well-known manner. Administration may be intramuscular, intravenous, intraperitoneal or by any other known method of delivering a pharmaceutical.

Therapeutic dosage of PN-2/$\beta$APP or an analog thereof when used intravenously in accordance with a method of the preferred embodiment for anti-coagulation is preferably in the range of 600 $\mu$g to 60 mg for a 70 kilogram adult per day, more preferably in the range of 3 mg to 12 mg active ingredient for a 70 kilogram adult per day. The total amount of active ingredient administered per day is preferably divided into two to four equal dosages per day. Example 34 provides one example of a therapeutic composition in accordance with the present invention.

EXAMPLE 34

An Anti-Coagulant Composition for Intravenous Injection 1 mg/ml: PN-2/$\beta$APP
balance: sterile H$_2$O

EXAMPLE 35

Anti-Coagulant Treatment of Phlebitis with PN-2/$\beta$APP

The composition of Example 34 is injected intravenously by five patients suffering from phlebitis of the leg. Five matched control patients receive a composition like Example 34, however, without active ingredient. The composition is taken two times per day for a period of three months. At the end of the three month period, the patients receiving the control composition have unchanged symptoms. In contrast, the patients receiving PN-2/$\beta$APP show increased blood flow through the leg relative to the start of this study.

EXAMPLE 36

Anti-Coagulant Treatment of Stroke with PN-2/$\beta$APP

The composition of Example 31 is taken intravenously by five patients who are recent victims of stroke. Five matched control patients receive the composition of Example 31 lacking active ingredient. The composition is taken two times daily for a two year period. By the end of the two year period, several patients of the control group will suffer repeat strokes, with some patients dying. In the same period fewer of the PN-2/$\beta$APP-treated group will have suffered a repeat stroke, and fewer will have died.

It will be appreciated that certain variations may suggest themselves to those skilled in the art. The foregoing detailed description is to be clearly understood as given by way of illustration, the spirit and scope of this invention being limited solely by the appended claims.

TABLE I

| | Immunopurification of PN-2/$\beta$APP | | | | | |
| STEP | VOLUME (ml) | PROTEIN (mg) | UNITS | SPECIFIC ACTIVITY (units/mg) | YIELD % | PURIFICATION -fold |
| --- | --- | --- | --- | --- | --- | --- |
| Conditioned medium | 4,000 | ~4,600 | 1,139 | 0.25 | 100 | |
| Dextran sulfate-Sepharose | 20 | 152 | 1,089 | 72 | 95 | 286 |
| mAbP2-1 | 8.5 | 0.175 | 861 | 4,920 | 76 | 19,680 |

TABLE I-continued

Immunopurification of PN-2/βAPP

| STEP | VOLUME (ml) | PROTEIN (mg) | UNITS | SPECIFIC ACTIVITY (units/mg) | YIELD % | PURIFICATION -fold |
|---|---|---|---|---|---|---|
| Sepharose | | | | | | |

TABLE II

Inhibition constants for proteases and PN-2/APP

| Protease (final molarity) | Substrate (final molarity) | $K_i$ (M) |
|---|---|---|
| Human factor XIa (5 nM) + heparin (10U/ml) | Pyro-Glu-Pro-Arg-p-nitroanilide hydrochloride (0.5 mM) | $5.5 \pm 0.3 \times 10^{-11}$ |
| Human factor XIa (5 nM) | Pyro-Glu-Pro-Arg-p-nitroanilide hydrochloride (0.5 mM) | $2.9 \pm 0.4 \times 10^{-10}$ |
| Bovine trypsin (5 nM) | Carbobenzoxy-Val-Gly-Arg-4-nitroanilide (0.5 mM) | $4.2 \pm 0.6 \pm 10^{-10}$ |
| Bovine chymotrypsin (2.5 nM) | N-Succinyl-Ala-Ala-Pro-Phe-p-nitroanilide (0.25 mM) | $1.6 \pm 0.4 \times 10^{-9}$ |
| Mouse EGF-BP (10 nM) | H-D-Pro-Phe-Arg-p-nitroanilide dihydrochloride (0.5 mM) | $5.8 \pm 0.3 \times 10^{-9}$ |
| Mouse NGF-γ (10 nM) | H-D-Pro-Phe-Arg-p-nitroanilide dihydrochloride (0.5 mM) | $9.1 \pm 1.2 \times 10^{-9}$ |
| Human skin chymase (20 nM) | N-Succinyl-Ala-Ala-Pro-Phe-p-nitroanilide (0.5 mM) | $2.0 \pm 1.0 \times 10^{-8}$ |
| Human plasmin (10 nM) | Tosyl-Gly-Pro-Lys-4-nitroanilide (0.5 mM) | $2.9 \pm 0.6 \times 10^{-8}$ |
| Human thrombin (10 nM) | Tosyl-Gly-Pro-Arg-4Onitroanilide (0.5 mM) | not inhibited |
| Human factor XIIa (20 nM) | D-HexahydroTyr-Gly-Arg-4-nitroanilide diacetate (1 mM) | not inhibited |
| Human factor Xa (10 nM) | N-Methoxycarbonyl-D-norLeu-Gly-Arg-4-nitroanilide (1 mM) | not inhibited |
| Human plasma kallikrein (20 nM) | H-D-Pro-Phe-Arg-p-nitroanilide dihydrochloride (1 mM) | not inhibited |
| Human tissue kallikrein (20 nM) | D-Val-cyclohexylAla-Arg-4-nitroanilide diacetate (0.5 mM) | not inhibited |
| Human urokinase (20 nM) | Benzoyl-β-Ala-Gly-Arg-4-nitroanilide (0.5 mM) | not inhibited |
| Human tissue plasminogen activator (20 nM) | N-Methylsulfonyl-D-Phe-Gly-Arg-4-nitroanilide (1 mM) | not inhibited |
| Porcine pancreatic elastase (20 nM) | N-Methoxysuccinyl-Ala-Ala-Pro-Val-p-nitroanilide (1 mM) | not inhibited |

TABLE III

Secretion of PN-2/βAPP by Activated Platelets

| | Washed Platelets | | Inhibitor-Treated Platelets | |
|---|---|---|---|---|
| Markers | Collagen (%) | Thrombin (%) | Collagen (%) | Thrombin (%) |
| PN-2/βAPP | 46.3 ± 7.7 | 53.7 ± 7.6 | 0 | 0 |
| ADP/ATP | 45 ± 16 | 68 ± 11 | 1.3 ± 1.3 | 0 |
| LA-PF4 | 52 ± 11 | 69 ± 6.2 | 0 | 0.4 ± 0.4 |
| LDH | 1.3 ± 1.3 | 0 | 0 | 0 |

TABLE IV

| Patient Population | Age (mean) | PN-2/βAPP Concentration μg/ml | Total Protein (mg/dl) | Specific Content PN-2/βAPP Total Protein (μg/mg) |
|---|---|---|---|---|
| Non-demented Controls (n = 16) | 62 ± 16 | 2.7 ± 0.7 | 40 ± 12 | 6.8 |
| Demented Controls (n = 18) | 69 ± 6 | 2.9 ± 1.0 | 39 ± 12 | 7.4 |
| Probable Alzheimer (n = 13) | 69 ± 9 | 0.8 ± 0.4 | 38 ± 11 | 2.1 |

TABLE V

Summary of quantitation of APP in cerebrospinal fluid samples from normals, HCHWA-D, and probable AD patients

| Patient group | Age (mean) | Cerebrospinal fluid APP levels | | Total cerebrospinal fluid protein (mg/dl)*** | Specific content total APP/total protein (μg/mg) |
|---|---|---|---|---|---|
| | | total APP (μg/ml)* | KPI-containing APP (μg/ml)** | | |
| Normals (N = 3) | 52 | 3.0 ± 0.2 | 0.084 ± 0.016 | 39 ± 15 | 7.7 |
| HCHWA-D (n = 3) | 57 | 0.7 ± 0.4 | 0.080 ± 0.029 | 42 ± 10 | 1.7 |
| Probable AD (n = 3) | 57 | 1.0 ± 0.3 | 0.077 ± 0.026 | 35 ± 5 | 2.8 |

*Cerebrospinal fluid total APP levels were determined by ELISAs and based on comparison to standard curve ELISAs with purified PN-II[APP].
**KPI-containing APP levels were determined by quantitative protease complex formation assays and based on comparsion to standard curve assays with purified PN-II[APP].
***Cerebrospinal fluid total protein content was determined using an automated ACA analyzer ACA analyzer (DuPont).

What is claimed is:

1. A method of diagnosing Alzheimer's Disease in a mammal, comprising the steps of:
   a. obtaining a sample of cerebrospinal fluid from said mammal;
   b. measuring the level of immunoreactivity toward a monoclonal antibody raised against native PN-2/βAPP in said sample;
   c. determining the level of immunoreactivity toward said antibody in a sample from a similar mammal, said similar mammal known to be free of Alzheimer's Disease; and
   d. comparing the level measured in step (b) with the level measured in step (c), wherein a lower level measured in step (b) than in step (c) indicates a likelihood of AD.

2. The method of claim 1, wherein step (b) comprises an ELISA assay.

3. The method of claim 1, wherein step (b) comprises an immunoblot assay.

4. The method of claim 1, wherein step (a) comprises collecting CSF by lumbar puncture.

5. The method of claim 1, wherein step (b) comprises measuring the level of immunoreactivity toward mAbP2-1.

6. A method of diagnosing Alzheimer's Disease in a mammal, comprising the steps of:
   a. obtaining a sample with a volume less than 100 μl of cerebrospinal fluid from said mammal;
   b. measuring the level of PN-2/βAPP in said sample;
   c. determining the level of PN-2/βAPP in a sample of the same volume of CSF from a similar mammal, said similar mammal known to be free of Alzheimer's Disease; and
   d. comparing the level measured in step (b) with the level measured in step (c), wherein a lower level measured in step (b) indicates a likelihood of AD.

7. The method of claim 6, wherein said sample has a volume in the range of 2 μl to 20 μl.

8. The method of claim 7, wherein said sample has a volume in the range of 2 μl to 10 μl.

9. The method of claim 6, wherein step (b) comprises an immunoassay for PN-2/βAPP.

10. The method of claim 9, wherein step (b) comprises measuring the level of immunoreactivity towards a monoclonal antibody raised against native PN-2/βAPP.

11. The method of claim 6, wherein step (b) comprises measuring the level of PN-2/βAPP in unconcentrated, nondialyzed CSF.

12. The method of claim 6, wherein step (b) comprises measuring the level of immunoreactivity toward a monoclonal antibody raised against native PN-2/βAPP.

13. The method of claim 12, wherein step (b) comprises measuring the level of immunoreactivity toward mABP2-1.

14. A method of diagnosing Alzheimer's Disease in a mammal that is manifesting symptoms of a dementia, wherein said method is capable of distinguishing between Alzheimer's Disease and a dementia not associated with cerebrovascular deposition of amyloid, comprising the steps of:
   a. obtaining a sample of cerebrospinal fluid from said mammal;
   b. measuring the level of immunoreactivity toward a monoclonal antibody raised against native PN-2/βAPP in said sample;
   c. determining the level of immunoreactivity toward said antibody in a sample from another similar mammal that is known to be suffering from a dementia not associated with cerebrovascular deposition of amyloid;
   d. comparing the level measured in step (b) with the level measured in step (c), wherein a lower level measured in step (b) indicates a likelihood of AD.

15. The method of claim 14, wherein the sample obtained in step (a) has a volume less than 100 μl.

16. The method of claim 15, wherein said sample has a volume in the range of 2 μl to 20 μl.

17. The method of claim 15, wherein said sample has a volume in the range of 2 μl to 10 μl.

18. The method of claim 14, wherein step (b) comprises an ELISA assay.

19. The method of claim 18, wherein step (b) comprises an ELISA using microtiter plates coated with a cationic substance.

20. The method of claim 14, wherein step (b) comprises an immunoblot assay.

21. The method of claim 14, wherein step (b) comprises collecting CSF by lumbar puncture.

22. The method of claim 14, wherein step (b) comprises measuring the level of immunoreactivity toward mAbP2-1.

23. A method of diagnosing a disease associated with cerebrovascular deposition of amyloid in a mammal, comprising:
   a. identifying an amyloid precursor protein which is the precursor to the amyloid deposited in the cerebrovasculature of mammals with said disease;
   b. obtaining a sample of cerebrospinal fluid from said mammal;
   c. measuring the level of immunoreactivity toward an antibody raised against said amyloid precursor protein in said sample;
   d. determining the level of immunoreactivity toward said antibody in a sample from a similar mammal, said similar mammal known to be free of said disease; and
   e. comparing the level measured in step (c) with the level measured in step (d), wherein a lower level measured in step (c) indicates a likelihood of said disease.

24. The method of claim 23, wherein said disease is Alzheimer's Disease or Hereditary Cerebral Hemorrhage With Amyloidosis, Dutch type and said amyloid precursor protein is PN-2/βAPP.

25. The method of claim 23, wherein said disease is Hereditary Cerebral Hemorrhage With Amyloidosis, Icelandic type and said amyloid precursor protein is cystatin-C.

26. The method of claim 23, wherein step (a) comprises:
   i) obtaining a sample of cerebrovascular amyloid deposits form a mammal suffering from said disease; and
   ii) identifying amyloid precursor proteins found therein.

27. The method of claim 26, wherein step (ii) comprises biochemical characterization of said sample of cerebrovascular deposits.

28. The method of claim 26, wherein step (ii) comprises:
   splitting said sample into a plurality of aliquots;
   screening said aliquots with a plurality of antibodies raised against a plurality precursor proteins associated with the deposition of amyloid;
   measuring the immunoreactivity of each said aliquot with each of said plurality of antibodies raised against a plurality precursor proteins associated with the deposition of amyloid; and
   identifying which particular amyloid precursor protein is contained in said sample by determining which of said aliquots exhibit significant levels of immunoreactivity with any of said plurality of antibodies.

29. A method of diagnosing a disease associated with cerebrovascular deposition of PN-2/βAPP in a mammal, comprising:

a. obtaining a sample of cerebrospinal fluid from said mammal;
b. determining the level of PN-2/βAPP lacking the Kunitz protease inhibitory domain in said sample;
c. determining the level of PN-2/βAPP lacking the Kunitz protease inhibitory domain in a sample from a similar mammal, said similar mammal known to be free said disease; and
d. comparing the level measured in step (b) with the level measured in step (c), wherein a lower level measured in step (b) indicates a likelihood of said disease.

30. The method of claim 29, wherein step (b) comprises determining the level of Kunitz protease inhibitory domain containing form of PN-2/βAPP and subtracting form the total level of PN-2/βAPP.

31. The method of claim 29, wherein the step of determining the level of Kunitz protease inhibitory domain containing form of PN-2/βAPP step comprises the performance of an assay for protease:PN-2/βAPP complex formation.

32. A method of detecting PN-2βAPP in a sample comprising measuring the level of immunoreactivity toward a monoclonal antibody raised against native PN-2/βAPP in said sample.

33. The method of claim 32, wherein the measuring step comprises measuring the level of immunoreactivity toward mAbP2-1.

34. The method of claim 32, wherein the sample contains proteins that are immunoreactive and nonimmunoreactive with a monoclonal antibody raised against native PN-2/βAPP, and said nonimmunoreactive protein is present in significant quantities in relation to said immunoreactive protein and the measuring step is capable of distinguishing between said immunoreactive protein and said nonimmunoreactive protein.

35. The method of claim 32, wherein the measuring step comprises measuring the level of immunoreactivity in a sample of CSF from a mammal.

* * * * *

UNITED STATES PATENT AND TRADEMARK OFFICE
CERTIFICATE OF CORRECTION

PATENT NO. : 5,270,165
DATED : December 14, 1993
INVENTOR(S) : William E. Van Nostrand, Dennis D. Cunningham, Steven I. Wagner It is certified that error appears in the above-indentified patent and that said Letters Patent is hereby corrected as shown below:

On the Title Page, Item[45], just before "Dec. 14, 1993" in the "Date of Patent" in the header, please add —*—.

On the Title Page, before Item [73], please add:
—[*] Notice: The portion of the term of this patent subsequent to May 25, 2010 has been disclaimed.—.

Signed and Sealed this

Twelfth Day of July, 1994

Attest:

BRUCE LEHMAN

Attesting Officer     Commissioner of Patents and Trademarks